(12) United States Patent
Leys et al.

(10) Patent No.: US 12,269,813 B2
(45) Date of Patent: *Apr. 8, 2025

(54) CRYSTALLINE FORM OF 1-(1-OXO-1,2-DIHYDROISOQUINOLIN-5-YL)-5-(TRIFLUOROMETHYL)-N-(2-(TRIFLUOROMETHYL)PYRIDIN-4-YL)-1H-PYRAZOLE-4-CARBOXAMIDE MONOHYDRATE

(71) Applicant: Janssen Pharmaceutica NV, Beerse (BE)

(72) Inventors: Carina Leys, Stabroek (BE); Kristof Leonard Kimpe, Beerse (BE); Robert Michael Geertman, Maarheeze (NL); Haojuan Wei, Changzhou (CN); Peng Zhou, Changzhou (CN)

(73) Assignee: Janssen Pharmaceutica NV, Beerse (BE)

( * ) Notice: Subject to any disclaimer, the term of this patent is extended or adjusted under 35 U.S.C. 154(b) by 725 days.

This patent is subject to a terminal disclaimer.

(21) Appl. No.: 17/431,447

(22) PCT Filed: Feb. 20, 2020

(86) PCT No.: PCT/EP2020/054485
§ 371 (c)(1),
(2) Date: Aug. 17, 2021

(87) PCT Pub. No.: WO2020/169736
PCT Pub. Date: Aug. 27, 2020

(65) Prior Publication Data
US 2022/0127249 A1    Apr. 28, 2022

(30) Foreign Application Priority Data
Feb. 22, 2019  (WO) ............... PCT/CN2019/075834

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
None
See application file for complete search history.

(56) References Cited

U.S. PATENT DOCUMENTS

| 8,389,544 B2 | 3/2013 | Wong et al. |
| 8,716,487 B2 | 5/2014 | Maywald et al. |
| 9,730,938 B2 | 8/2017 | Kuo et al. |

(Continued)

FOREIGN PATENT DOCUMENTS

| TW | 201609740 A | 3/2016 |
| WO | WO 2004/098515 A2 | 11/2004 |

(Continued)

OTHER PUBLICATIONS

CHEMCATS Registry No. 1907875-04-0, 1H-Pyrazole-4-carboxamide, N-(2-chloro-3-pyridinyl)-5-methyl-1-(2-quinolinyl)—May 11, 2016—Ref. 1.

(Continued)

*Primary Examiner* — Jeffrey S Lundgren
*Assistant Examiner* — Anthony Joseph Seitz

(57) ABSTRACT

The present invention relates to a crystalline form of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate, and processes for preparation thereof. The crystalline form and compositions thereof are useful in the treatment of MALT-1 related diseases.

13 Claims, 12 Drawing Sheets

(56) References Cited

U.S. PATENT DOCUMENTS

| | | | |
|---|---|---|---|
| 9,814,721 | B2 | 11/2017 | Buggy et al. |
| 9,815,842 | B2 | 11/2017 | Soldermann et al. |
| 10,882,841 | B2 | 1/2021 | Xue et al. |
| 10,954,214 | B2 * | 3/2021 | Lu .................. C07D 491/04 |
| 2018/0071295 | A1 | 3/2018 | Kuo et al. |
| 2018/0311153 | A1 | 11/2018 | Buggy et al. |
| 2020/0009135 | A1 | 1/2020 | Albertella et al. |
| 2021/0001733 | A1 | 1/2021 | Meins et al. |
| 2021/0052596 | A1 | 2/2021 | Mempel et al. |
| 2022/0056012 | A1 * | 2/2022 | Kimpe .................. A61K 9/284 |

FOREIGN PATENT DOCUMENTS

| | | | |
|---|---|---|---|
| WO | WO 2017/081641 | A1 | 5/2017 |
| WO | WO 2018/141749 | A1 | 8/2018 |
| WO | WO 2021/138298 | A2 | 7/2021 |

OTHER PUBLICATIONS

CHEMCATS Registry No. 1907028-26-5, 1H-Pyrazole-4-carboxamide, N-(3-chloro-4-methoxphenyl)-5-methyl-1-(2-quinolinyl)—May 10, 2016—Ref. 2.

CHEMCATS Registry No. 1898933-19-1, 1H-Pyrazole-4-carboxamide, 5-methyl-N-3-pyridinyl-1-(2-quinolinyl)—Apr. 27, 2016—Ref. 3.

Nagel, D., et al., "Combinatorial BTK and MALT1 inhibition augments killing of CD79 mutant diffuse large B cell lymphoma", (2015), Oncotarget, vol. 6, No. 39, pp. 1-11.

Philippar, U., et al., "Abstract 5690: Discovery of JNJ-67856633: A novel, first-in-class MALT1 protease inhibitor for the treatment of B cell lymphomas", Cancer Research (2020), Proceedings of the Annual Meeting of the American Association for Cancer Research, vol. 80, issue 16 suppl, pp. 1-5.

* cited by examiner

CRYSTALLINE FORM OF 1-(1-OXO-1,2-DIHYDROISOQUINOLIN-5-YL)-5-(TRIFLUOROMETHYL)-N-(2-(TRIFLUOROMETHYL)PYRIDIN-4-YL)-1H-PYRAZOLE-4-CARBOXAMIDE MONOHYDRATE

FIELD OF THE INVENTION

The present invention relates to a crystalline form of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate. This crystalline form may be useful for the treatment of a disease, syndrome, condition, or disorder, particularly a MALT1-related disease, syndrome, condition, or disorder, including but not limited to, cancer and immunological diseases. The invention also relates to pharmaceutical compositions comprising such a crystalline form, to processes to prepare such a crystalline form, and to the use of such crystalline form or pharmaceutical composition for the treatment of cancer and autoimmunological diseases, syndromes, disorders, or conditions associated with MALT1 inhibitors.

BACKGROUND OF THE INVENTION

MALT1 (mucosa-associated lymphoid tissue lymphoma translocation 1) is a key mediator of the classical NFKB signaling pathway. MALT1 is the only human paracaspase and transduces signals from the B cell receptor (BCR) and T cell receptor (TCR). MALT1 is the active subunit of the CBM complex which is formed upon receptor activation. The CBM complex consists of multiple subunits of three proteins: CARD11 (caspase recruitment domain family member 11), BCL10 (B-cell CLL/Lymphoma 10) and MALT1. MALT1 affects NFKB signaling by two mechanisms: firstly, MALT1 functions as a scaffolding protein and recruits NFKB signaling proteins such as TRAF6, TAB-TAK1 or NEMO-IKKα/β; and secondly, MALT1, as a cysteine protease, cleaves and thereby deactivates negative regulators of NFKB signaling, such as RelB, A20 or CYLD. The ultimate endpoint of MALT1 activity is the nuclear translocation of the FKB transcription factor complex and activation of FKB signaling (Jaworski et al., Cell Mol Life Science 2016. 73, 459-473).

Constitutive activation of FKB signaling is the hallmark of ABC-DLBCL (Diffuse Large B cell Lymphoma of the Activated B Cell-like subtype), the more aggressive form of DLBCL. DLBCL is the most common form of non-Hodgkin's lymphoma (NHL), accounting for approximately 25% of lymphoma cases while ABC-DLBCL comprises approximately 40% of DLBCL. NFKB pathway activation is driven by mutations of signaling components, such as CD79A/B, CARD11, MYD88 or A20, in ABC-DLBCL patients (Staudt, Cold Spring Harb Perspect Biol 2010, 2; Lim et al, Immunol Rev 2012, 246, 359-378).

The use of BTK inhibitors, for example Ibrutinib, provides clinical proof-of-concept that inhibiting NFKB signaling in ABC-DLBCL is efficacious. MALT1 is downstream of BTK in the NFKB signaling pathway and a MALT1 inhibitor could target ABC-DLBCL patients not responding to Ibrutinib, mainly patients with CARD11 mutations, as well as treat patients that acquired resistance to Ibrutinib.

Small molecule tool compound inhibitors of MALT1 protease have demonstrated efficacy in preclinical models of ABC-DLBCL (Fontan et al., Cancer Cell 2012, 22, 812-824; Nagel et al., Cancer Cell 2012, 22, 825-837). Interestingly, covalent catalytic site and allosteric inhibitors of MALT1 protease function have been described, suggesting that inhibitors of this protease may be useful as pharmaceutical agents (Demeyer et al., Trends Mol Med 2016, 22, 135-150).

The chromosomal translocation creating the API2-MALT1 fusion oncoprotein is the most common mutation identified in MALT (mucosa-associated lymphoid tissue) lymphoma. API2-MALT1 is a potent activator of the NFKB pathway (Rosebeck et al., World J Biol Chem 2016, 7, 128-137). API2-MALT1 mimics ligand-bound TNF receptor, promotes TRAF2-dependent ubiquitination of RIP1 which acts as a scaffold for activating canonical NFKB signaling. Furthermore, API2-MALT1 has been shown to cleave and generate a stable, constitutively active fragment of NFKB-inducing kinase (NIK) thereby activating the non-canonical FKB pathway (Rosebeck et al., Science, 2011, 331, 468-472).

In addition to lymphomas, MALT1 has been shown to play a critical role in innate and adaptive immunity (Jaworski M, et al., Cell Mol Life Sci. 2016). MALT1 protease inhibitor can attenuate disease onset and progression of mouse experimental allergic encephalomyelitis, a mouse model of multiple sclerosis (Mc Guire et al., J. Neuroinflammation 2014, 11, 124). Mice expressing catalytically inactive MALT1 mutant showed loss of marginal zone B cells and B1B cells and general immune deficiency characterized as decreased T and B cell activation and proliferation. However, those mice also developed spontaneous multi-organ autoimmune inflammation at the age of 9 to 10 weeks. It is still poorly understood why MALT1 protease dead knock-in mice show a break of tolerance while conventional MALT1 KO mice do not. One hypothesis suggests the unbalanced immune homeostasis in MALT1 protease dead knock-in mice may be caused by incomplete deficiency in T and B cell but severe deficiency of immunoregulatory cells (Jaworski et al., EMBO J. 2014; Gewies et al., Cell Reports 2014; Bornancin et al., J. Immunology 2015; Yu et al., PLOS One 2015). Similarly, MALT deficiency in humans has been associated with combined immunodeficiency disorder (McKinnon et al., J. Allergy Clin. Immunol. 2014, 133, 1458-1462; Jabara et al., J. Allergy Clin. Immunol. 2013, 132, 151-158; Punwani et al., J. Clin. Immunol. 2015, 35, 135-146). Given the difference between genetic mutation and pharmacological inhibition, a phenotype of MALT1 protease dead knock-in mice might not resemble that of patients treated with MALT1 protease inhibitors. A reduction of immunosuppressive T cells by MALT1 protease inhibition may be beneficial to cancer patients by potentially increasing antitumor immunity.

Thus, MALT1 inhibitors may provide a therapeutic benefit to patients suffering from cancer and/or immunological diseases.

WO 2018/119036, which is incorporated herein by reference, discloses compounds that inhibit MALT1, including 1-(1-oxo-1,2-dihydroisoquinolin-5-yl)-5-(trifluoromethyl)-N-[2-(trifluoromethyl)pyridin-4-yl]-1H-pyrazole-4-carboxamide (recited in WO 2018/119036 as compound 158).

There is a need to provide alternate forms of 1-(1-oxo-1,2-dihydroisoquinolin-5-yl)-5-(trifluoromethyl)-N-[2-(trifluoromethyl)pyridin-4-yl]-1H-pyrazole-4-carboxamide.

SUMMARY OF THE INVENTION

The present invention is directed to crystalline Form III of 1-(1-oxo-1,2 dihydroisoquinolin-5-yl)-5-(trifluoromethyl)-N-(2-(trifluoromethyl)pyridin-4-yl)-1H-pyrazole-4-carboxamide (Compound A) monohydrate:

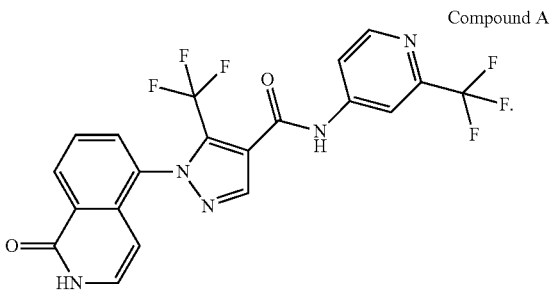 [SMILES: O=C(Nc1ccnc(C(F)(F)F)c1)c1cnn(-c2cccc3c(=O)[nH]ccc23)c1C(F)(F)F]

Compound A

A person of ordinary skill in the art would recognize that other tautomeric arrangements of Compound A are possible. For example, it is understood that

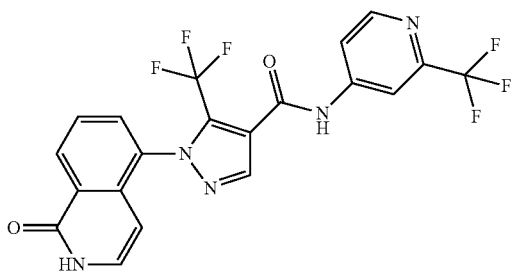 [SMILES: O=C(Nc1ccnc(C(F)(F)F)c1)c1cnn(-c2cccc3c(=O)[nH]ccc23)c1C(F)(F)F]

can occur in another tautomeric arrangement

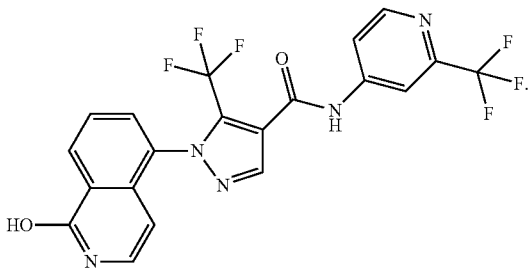 [SMILES: O=C(Nc1ccnc(C(F)(F)F)c1)c1cnn(-c2cccc3c(O)nccc23)c1C(F)(F)F]

Within the context of this invention, in a crystalline Form of Compound A, Compound A may be in either one of the above tautomeric arrangements or may be a mixture thereof, the exact tautomeric arrangement being unknown. For simplicity, only one possible tautomeric arrangement of the groups of Compound A is utilized in describing the compounds, but it should be clear to a person of ordinary skill in the art that in a crystalline Form of Compound A, such as crystalline Form III of Compound A monohydrate, Compound A may be in one of the above tautomeric arrangements or may be a mixture thereof.

An embodiment of the present invention is directed to a pharmaceutical composition comprising crystalline Form III of Compound A monohydrate.

The present invention also provides a pharmaceutical composition comprising, consisting of and/or consisting essentially of a pharmaceutically acceptable carrier, a pharmaceutically acceptable excipient, and/or a pharmaceutically acceptable diluent and crystalline Form III of Compound A monohydrate.

Also provided are processes for making a pharmaceutical composition comprising, consisting of, and/or consisting essentially of admixing crystalline Form III of Compound A monohydrate, and a pharmaceutically acceptable carrier, a pharmaceutically acceptable excipient, and/or a pharmaceutically acceptable diluent.

The present invention further provides methods for treating or ameliorating a disease, syndrome, condition, or disorder in a subject, including a mammal and/or human in which the disease, syndrome, condition, or disorder is affected by the inhibition of MALT1, including but not limited to, cancer and/or immunological diseases, using crystalline Form III of Compound A monohydrate.

The present invention is also directed to the use of crystalline Form III of Compound A monohydrate in the preparation of a medicament wherein the medicament is prepared for treating a disease, syndrome, disorder or condition that is affected by the inhibition of MALT1, such as cancer and/or immunological diseases.

Exemplifying the invention are methods of treating a disease, syndrome, condition, or disorder mediated by MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor), comprising, consisting of, and/or consisting essentially of, administering to a subject in need thereof a therapeutically effective amount of crystalline Form III of Compound A monohydrate.

In another embodiment, the present invention is directed to crystalline Form III of Compound A monohydrate for use as a medicament.

In another embodiment, the present invention is directed to crystalline Form III of Compound A monohydrate for use in the treatment of a disease, syndrome, condition, or disorder affected by the inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the present invention is directed to a composition comprising crystalline Form III of Compound A monohydrate for the treatment of a disease, syndrome, condition, or disorder affected by inhibition of MALT1, selected from the group consisting of lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumour).

In another embodiment, the present invention is directed to a composition comprising crystalline Form III of Compound A monohydrate for the treatment of a disease, syndrome, condition, or disorder affected by inhibition of MALT1, selected from the group consisting of diffuse large B-cell lymphoma (DLBCL), mantle cell lymphoma (MCL), follicular lymphoma (FL), and mucosa-associated lymphoid tissue (MALT) lymphoma.

An embodiment of the present invention is directed to a composition comprising crystalline Form III of Compound A monohydrate for the treatment of immunological diseases that are affected by the inhibition of MALT1, including but not limited to, autoimmune and inflammatory disorders, e.g. arthritis, inflammatory bowel disease, gastritis, ankylosing spondylitis, ulcerative colitis, pancreatitis, Crohn's disease, celiac disease, multiple sclerosis, systemic lupus erythematosus, lupus nephritis, rheumatic fever, gout, organ or transplant rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

In another embodiment, the present invention is directed to a composition comprising crystalline Form III of Compound A monohydrate for the treatment of a disease, syndrome, condition, or disorder affected by inhibition of MALT1, selected from the group consisting of rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD).

The present invention is also directed to the preparation of crystalline Form III of Compound A monohydrate.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific disclosure of the drawings. In the drawings.

DETAILED DESCRIPTION OF THE INVENTION

Figure 1:
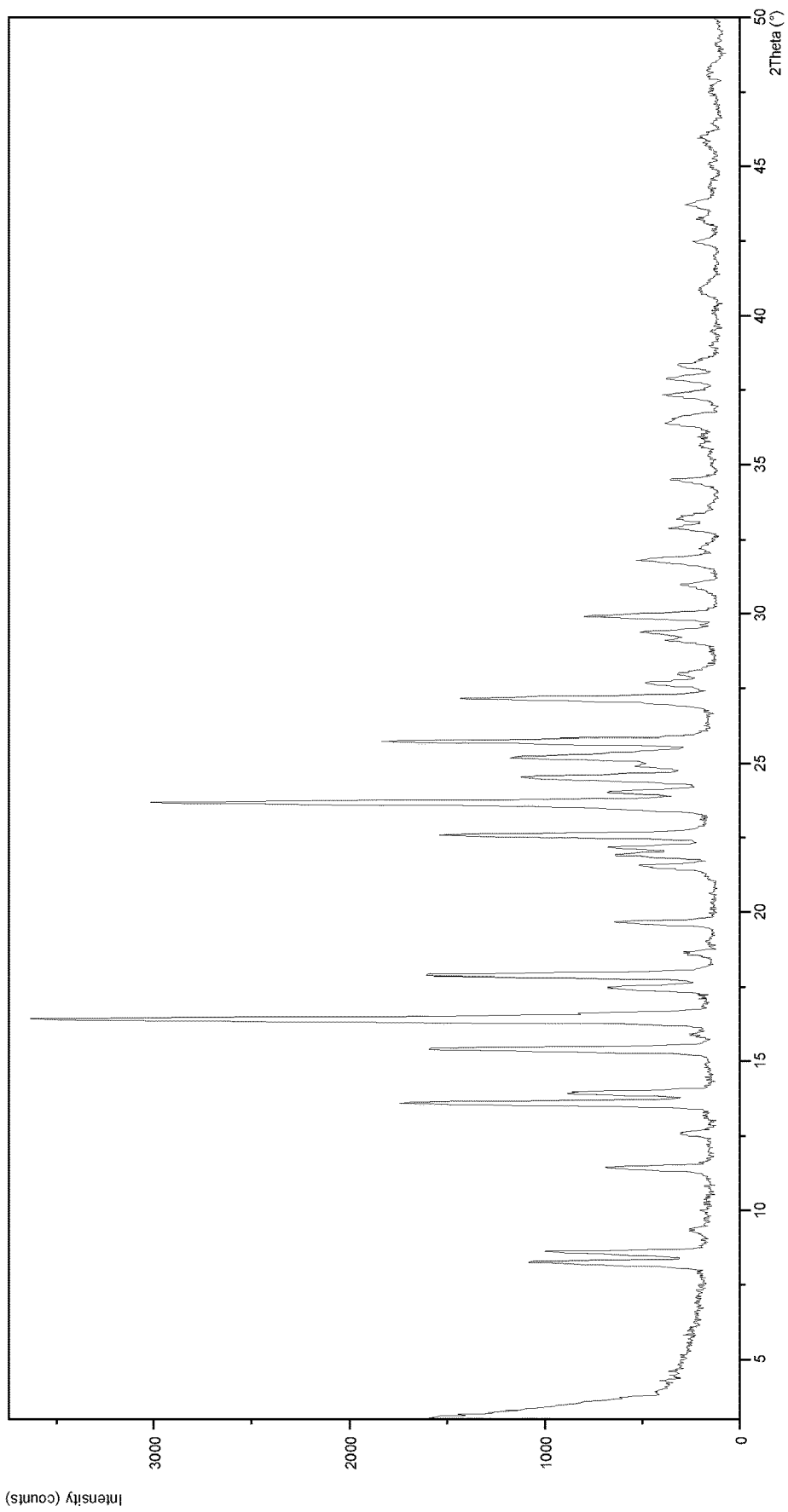
FIG. 1 is an X-ray powder diffraction pattern (XRPD) pattern of Compound A monohydrate, Form III.

The disclosure may be more fully appreciated by reference to the following description, including the following glossary of terms and the concluding examples. It is to be appreciated that certain features of the disclosed crystalline form, compositions and methods which are, for clarity, described herein in the context of separate aspects, may also be provided in combination in a single aspect. Conversely, various features of the disclosed crystalline form, compositions and methods that are, for brevity, described in the context of a single aspect, may also be provided separately or in any sub-combination.

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and claims of this specification, the words "comprise" and "contain" and variations of the words, for example "comprising" and "comprises", mean "including but not limited to", and are not intended to (and do not) exclude other components.

For the purposes of this disclosure, the terms "crystalline form" and "polymorph" are synonymous. Characterizing information for crystalline forms is provided herein. It should be understood that the determination of a particular form can be achieved using any portion of the characterizing information that one skilled in the art would recognize as sufficient for establishing the presence of a particular form. For example, even a single distinguishing peak can be sufficient for one skilled in the art to appreciate that a particular form is present.

The term "isolated form" refers to a compound present in a form which is separate from any mixture with another compound(s), solvent system or biological environment. In an embodiment of the present invention, the crystalline form is present in an isolated form.

The term "room temperature" (RT) refers to a temperature of from about 15° C. to about 30° C., in particular from about 20° C. to about 30° C. Preferably, room temperature is a temperature of about 25° C.

When a crystalline form is identified using one or more XRPD peaks given as angles 2θ (two theta), each of the 2θ values is understood to mean the given value±0.2 degrees, unless otherwise expressed.

When a crystalline form is identified using one or more temperatures from a differential scanning calorimetry thermogram (DSC) curve (e.g., onset of endothermic transition, melt, etc.), each of the temperature values is understood to mean the given value±2° C., unless otherwise expressed.

The term "seeding" refers to the addition of crystalline material to a solution or mixture to initiate crystallisation or recrystallisation.

Compound A may exist as a solvate. A "solvate" may be a solvate with water (i.e., a hydrate) or with a common organic solvent.

The crystalline Form III of Compound A monohydrate may be provided in a substantially pure form, wherein the mole percent of impurities in the isolated crystalline form is less than about 5 mole percent, preferably less than about 2 mole percent, more preferably, less than about 0.5 mole percent, most preferably, less than about 0.1 mole percent. In an embodiment of the present invention, the crystalline Form III of Compound A monohydrate is present as a substantially pure form.

Also provided herein is Compound A as a mixture of crystalline Form III of Compound A monohydrate and one or more additional forms of Compound A or a solvate thereof. At least a particular weight percentage of Compound A may be crystalline Form III of Compound A monohydrate. Particular weight percentages include 10%, 20%, 30%, 40%, 50%, 60%, 70%, 80%, 85%, 90%, 95%, 96%, 97%, 98%, 99%, 99.5% and 99.9%. When a particular percentage by weight of the compound is crystalline monohydrate Form III, the remainder of the compound may be an amorphous form of Compound A, crystalline Compound A hydrate Form I, one or more other crystalline forms of Compound A, or mixtures thereof.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The term "subject" refers to an animal, preferably a mammal, most preferably a human, who has been the object of treatment, observation or experiment.

The term "therapeutically effective amount" refers to an amount of an active compound or pharmaceutical agent, including a crystalline form of the present invention, which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease.

In one embodiment, the term "therapeutically effective amount" refers to the amount of a crystalline form of the present invention that, when administered to a subject, is effective to (1) at least partially alleviate, inhibit, prevent, and/or ameliorate a condition, or a disorder or a disease (i) mediated by MALT1; or (ii) associated with MALT1 activity; or (iii) characterized by activity (normal or abnormal) of MALT1; or (2) reduce or inhibit the activity of MALT1; or (3) reduce or inhibit the expression of MALT1; or (4) modify the protein levels of MALT1.

The term "composition" refers to a product that includes the specified ingredients in therapeutically effective amounts, as well as any product that results, directly, or indirectly, from combinations of the specified ingredients in the specified amounts.

The term "MALT1-mediated" refers to any disease, syndrome, condition, or disorder that might occur in the absence of MALT1 but can occur in the presence of MALT1. Suitable examples of a disease, syndrome, condition, or disorder mediated by MALT1 include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocytic leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head and neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumour).

As used herein, the term "MALT1 inhibitor" refers to an agent that inhibits or reduces at least one condition, symptom, disorder, and/or disease of MALT1.

As used herein, unless otherwise noted, the term "affect" or "affected" (when referring to a disease, syndrome, condition or disorder that is affected by the inhibition of MALT1) includes a reduction in the frequency and/or severity of one or more symptoms or manifestations of said disease, syndrome, condition or disorder; and/or includes the prevention of the development of one or more symptoms or manifestations of said disease, syndrome, condition or disorder or the development of the disease, condition, syndrome or disorder.

As used herein, the term "treat", "treating", or "treatment" of any disease, condition, syndrome or disorder refers, in one embodiment, to ameliorating the disease, condition, syndrome or disorder (i.e. slowing or arresting or reducing the development of the disease or at least one of the clinical symptoms thereof). In another embodiment, "treat", "treating", or "treatment" refers to alleviating or ameliorating at least one physical parameter including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

Crystalline Form I of Compound A Hydrate 1-(1-oxo-1,2-dihydroisoquinolin-5-yl)-5-(trifluoromethyl)-N-[2-(trifluoromethyl)pyridin-4-yl]-1H-pyrazole-4-carboxamide has the following structure and is identified herein as "Compound A."

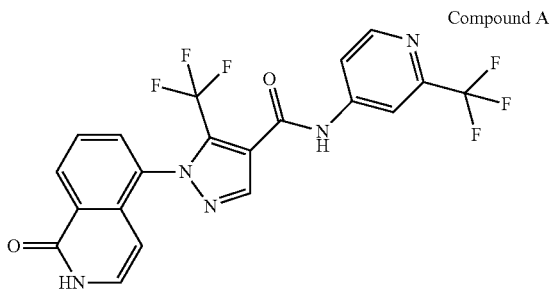 [SMILES: O=C(Nc1ccnc(C(F)(F)F)c1)c1cnn(-c2cccc3c(=O)[nH]ccc23)c1C(F)(F)F]

Compound A

Compound A may be prepared, for example, by analogy to the procedure as described in Example 158 of WO 2018/119036, which is incorporated herein by reference. The procedure of Example 158 has been determined as providing crystalline Form I of Compound A hydrate. Form I demonstrates hygroscopic behaviour.

Form I may be characterised by an X-ray powder diffraction pattern. The X-ray powder diffraction pattern may be obtained using copper K-alpha X-rays at a wavelength of 1.5406.

The X-ray powder diffraction pattern comprises peaks at 8.4, 12.7, 13.3 and 16.7 degrees two theta±0.2 degrees two theta. The X-ray powder diffraction pattern may further comprise at least one peak selected from 6.7, 10.0, 10.7, 12.0, 12.3, 13.5, 14.1, 14.6, 15.4, 15.6, 16.0, 18.1, 18.4, 19.2, 20.0, 20.3, 21.1, 22.0 and 24.9 degrees two theta±0.2 degrees two theta.

Form I may further be characterized by an X-ray powder diffraction pattern having four, five, six, seven, eight, nine or more peaks selected from those peaks identified in Table 1.

Form I may further be characterized by an X-ray powder diffraction pattern comprising those peaks identified in Table 1, wherein the relative intensity of the peaks is greater than about 2%, preferably greater than about 5%, more preferably greater than about 10%, more preferably greater than about 15%.

Figure 7:
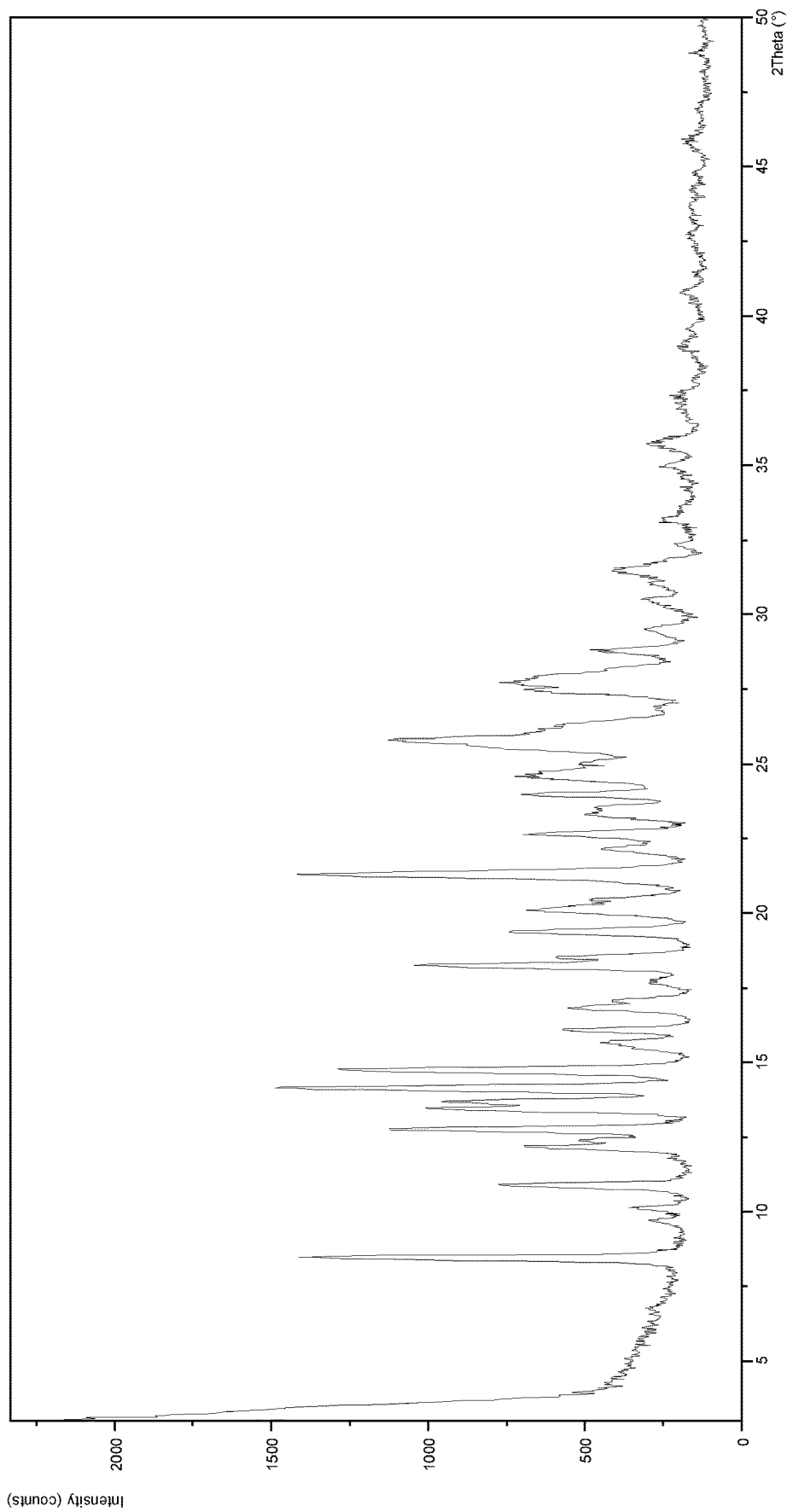
FIG. 7 is an XRPD pattern of Compound A hydrate, Form I.

Form I may further be characterized by an X-ray powder diffraction pattern substantially as depicted in FIG. 7.

Figure 8:
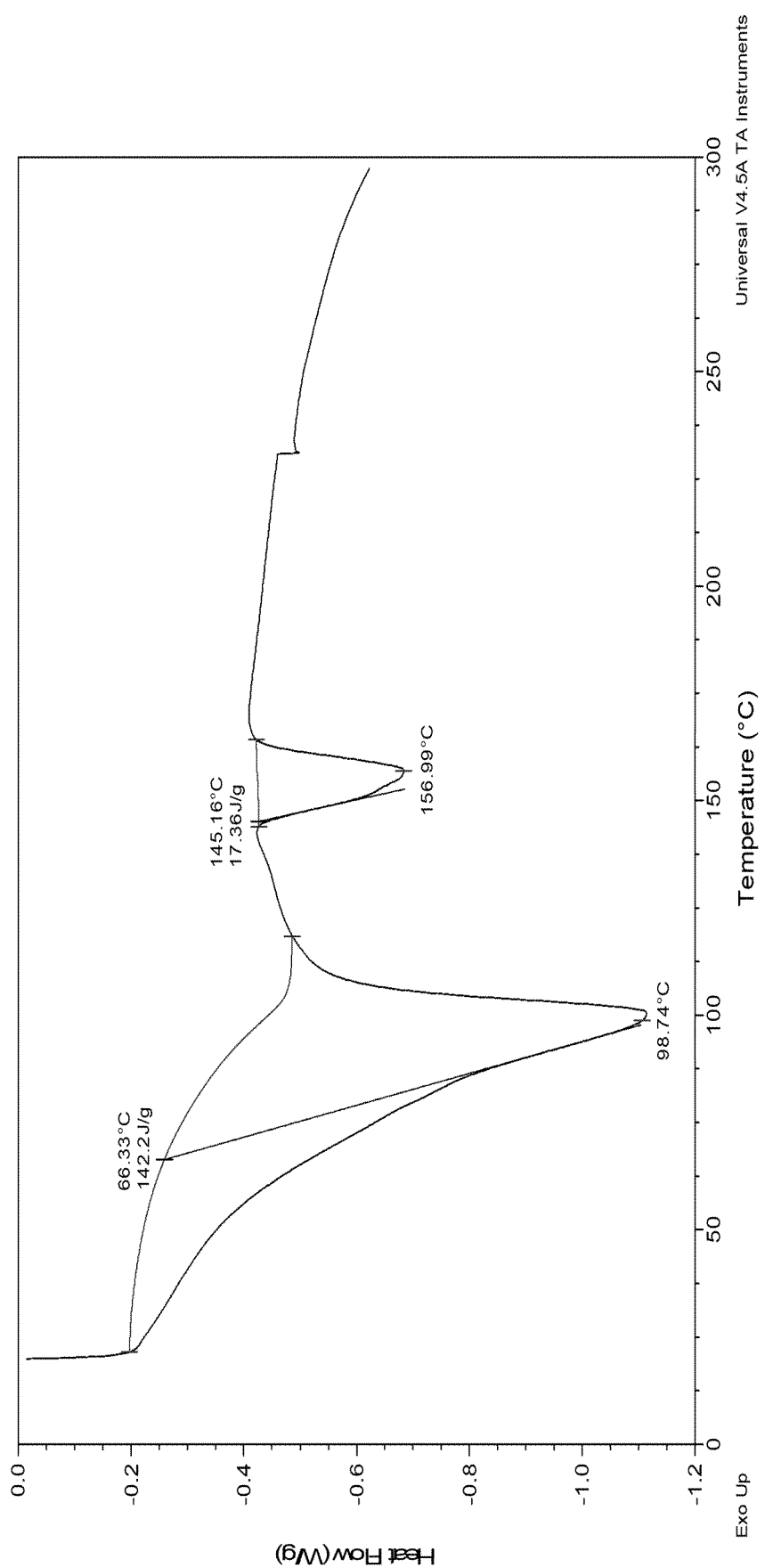
FIG. 8 is an DSC thermogram of Compound A hydrate, Form I.

Form I may also be characterized by a differential scanning calorimetry thermogram (DSC) comprising an endotherm with an onset temperature of 66° C. and a peak temperature at 99° C. The DSC may comprise a second endotherm with onset temperature of 145° C. and a peak temperature of 157° C. Form I may be characterised by a DSC substantially as depicted in FIG. 8.

Figure 9:
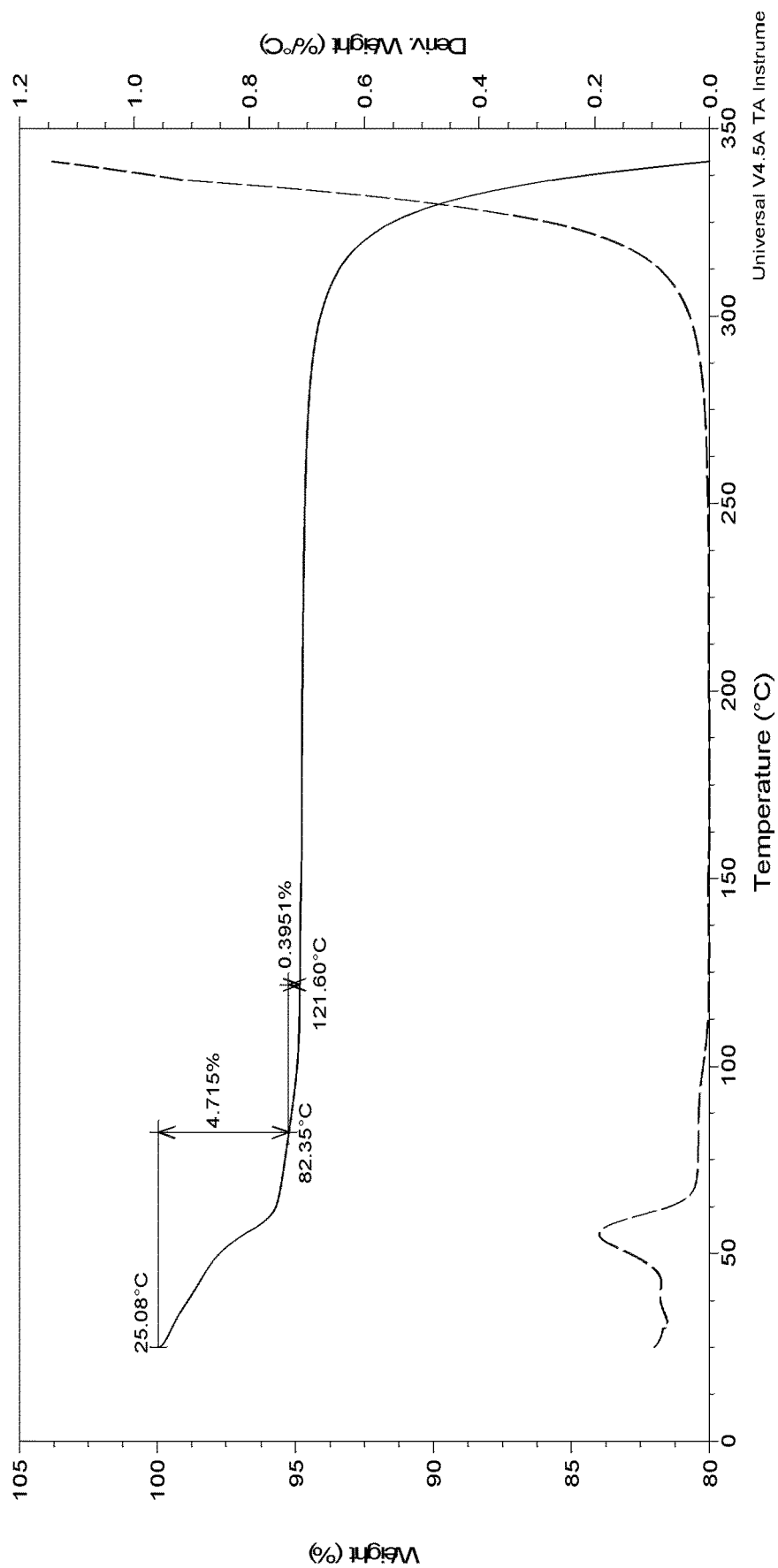
FIG. 9 is an TGA curve of Compound A hydrate, Form I.

Form I may further be characterized by thermal gravimetric analysis (TGA). Form I may exhibit a TGA curve substantially as depicted in FIG. 9.

Figure 10:
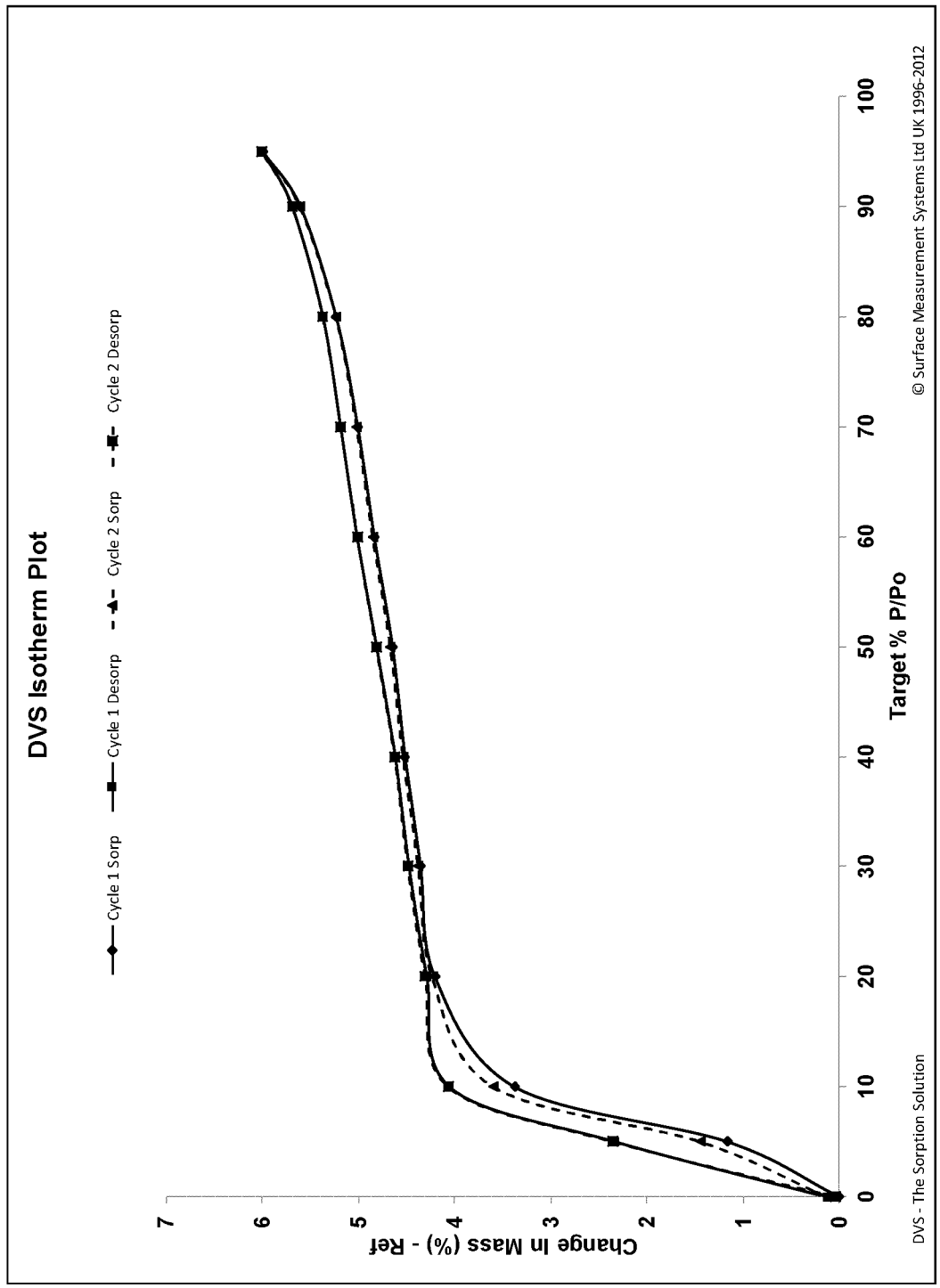
FIG. 10 is an DVS isotherm plot of Compound A hydrate, Form I.

Form I may further be characterized by dynamic vapor sorption (DVS). Form I may exhibit a DVS isotherm plot substantially as depicted in FIG. 10.

Crystalline Form III of Compound A Monohydrate

Form III demonstrates non-hygroscopic behaviour (less than 0.2% water uptake at 80% relative humidity). Unlike hydrate Form I, Form III avoids loss of water at low relative humidity (e.g. a relative humidity of 20% or less). These are desirable properties in active pharmaceutical ingredients, in particular those intended for solid dosage forms. Accurate quantities of Compound A may be dispensed and weighing errors avoided (for example, when preparing formulations or dosage forms), when water content variation is avoided.

Form III may be characterised by an X-ray powder diffraction pattern. The X-ray powder diffraction pattern may be obtained using copper K-alpha X-rays at a wavelength of 1.5406.

The X-ray powder diffraction pattern comprises peaks at 16.4, 23.7 and 25.7 degrees two theta±0.2 degrees two theta. The X-ray powder diffraction pattern may further comprise peaks at 13.6, 17.9, 22.6, 24.5, 25.2 and 27.1 degrees two theta±0.2 degrees two theta. The X-ray powder diffraction pattern may further comprise at least one peak selected from 8.3, 8.6, 11.5, 14.0, 15.4, 17.5, 19.7, 22.0, 22.2, 24.0 and 29.9 degrees two theta±0.2 degrees two theta.

The X-ray powder diffraction pattern may comprise peaks at 8.3, 8.6, 11.5, 13.6, 14.0, 15.4, 16.4, 17.5, 17.9, 19.7, 22.6, 23.7, 24.5, 25.2, 25.7, and 27.1 degrees two theta±0.2 degrees two theta.

The X-ray powder diffraction pattern may comprise peaks at 11.5, 16.4, 19.7, 23.7 and 25.7 degrees two theta±0.2 degrees two theta.

Form III may further be characterized by an X-ray powder diffraction pattern having four, five, six, seven, eight, nine or more peaks selected from those peaks identified in Table 2. Compound A monohydrate, Form III may further be characterized by an X-ray powder diffraction pattern comprising those peaks identified in Table 2, wherein the relative intensity of the peaks is greater than about 2%, preferably greater than about 5%, more preferably greater than about 10%, more preferably greater than about 15%. However, a skilled person will realize that the relative intensity of the peaks may vary between different samples and different measurements on the same sample.

Form III may further be characterized by an X-ray powder diffraction pattern substantially as depicted in FIG. 1.

Figure 2:
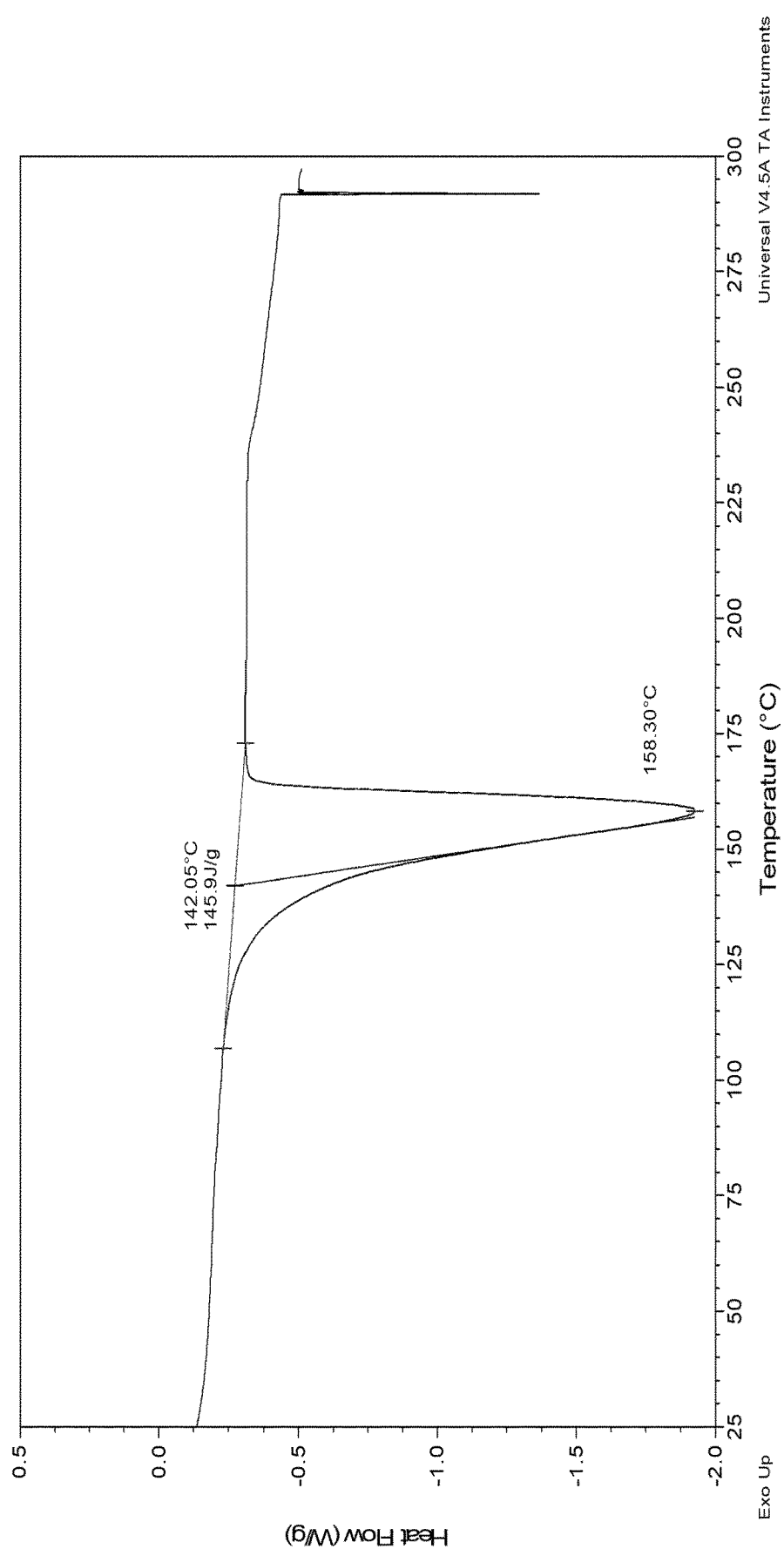
FIG. 2 is a differential scanning calorimetry (DSC) thermogram of Compound A monohydrate, Form III.

Form III may also be characterized by a differential scanning calorimetry thermogram (DSC) comprising an endotherm with an onset temperature of 142° C. and a peak temperature at 158° C. Form III may be characterised by a differential scanning calorimetry thermogram substantially as depicted in FIG. 2.

Figure 3:
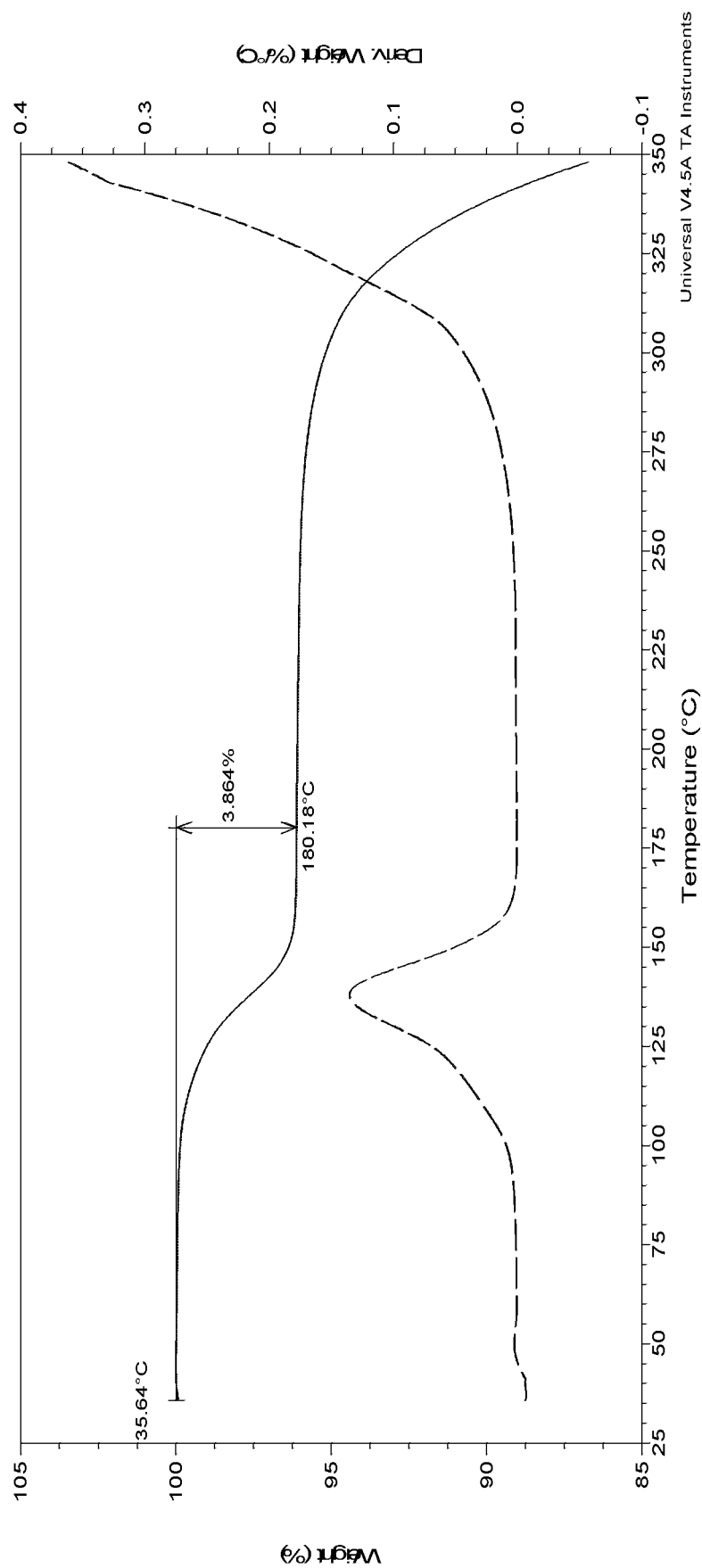
FIG. 3 is a thermogravimetric analysis (TGA) curve of Compound A monohydrate, Form III.

Form III may further be characterized by thermal gravimetric analysis (TGA). Form III may exhibit a TGA curve substantially as depicted in FIG. 3.

Figure 4:
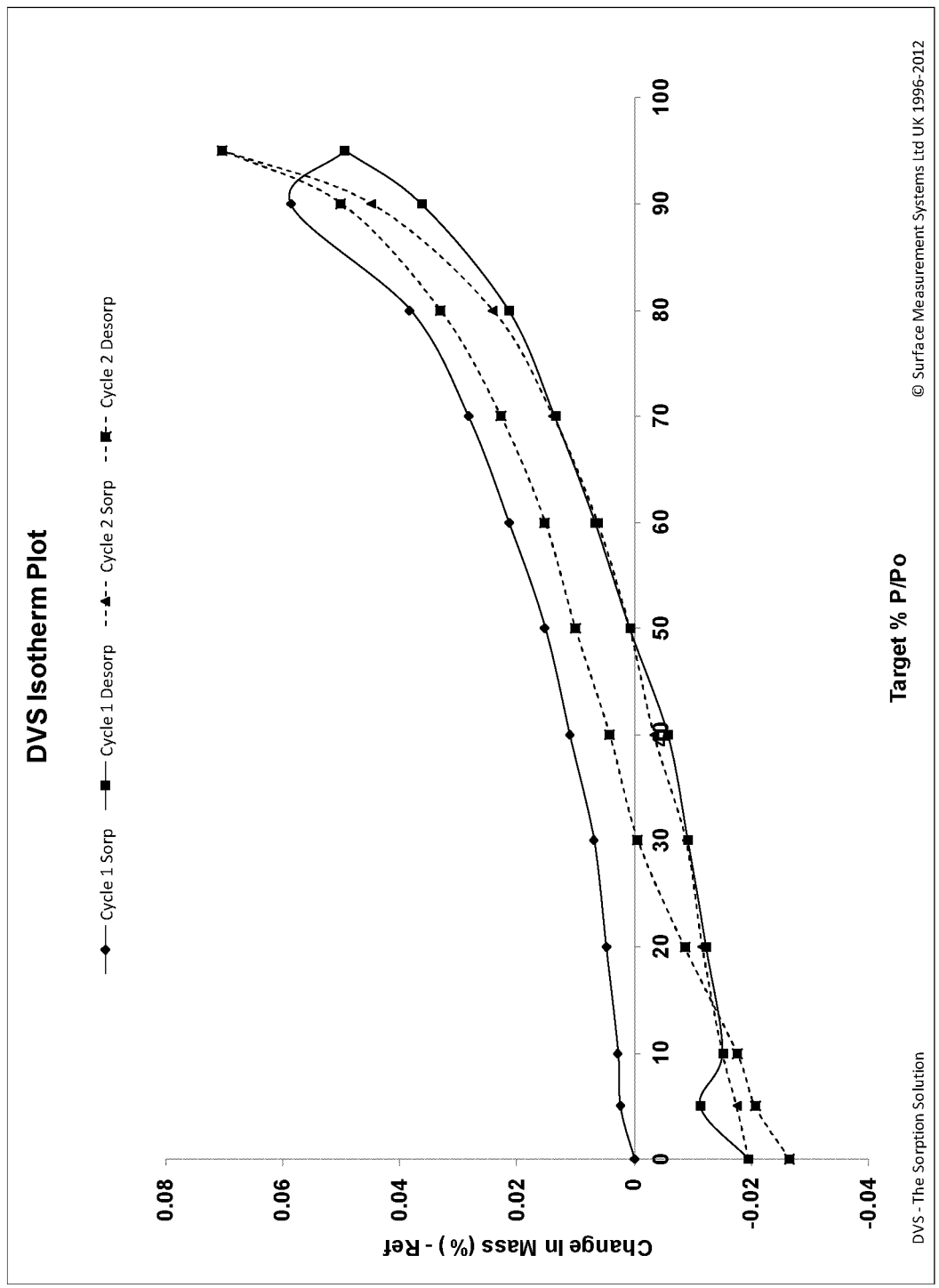
FIG. 4 is a dynamic vapor sorption (DVS) isotherm plot of Compound A monohydrate, Form III.
Figure 5:
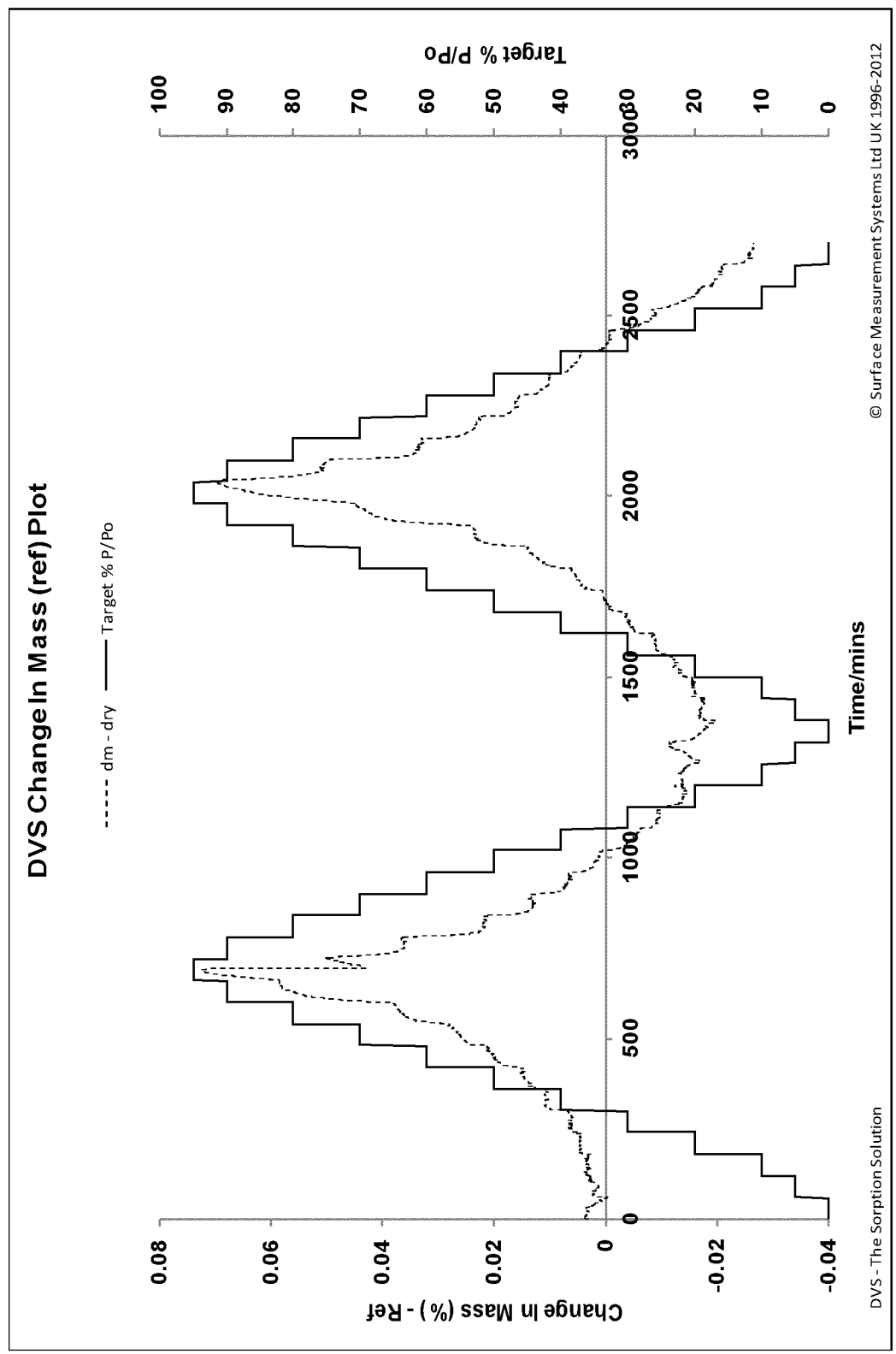
FIG. 5 is an DVS change in mass plot of Compound A monohydrate, Form III.
Figure 6:
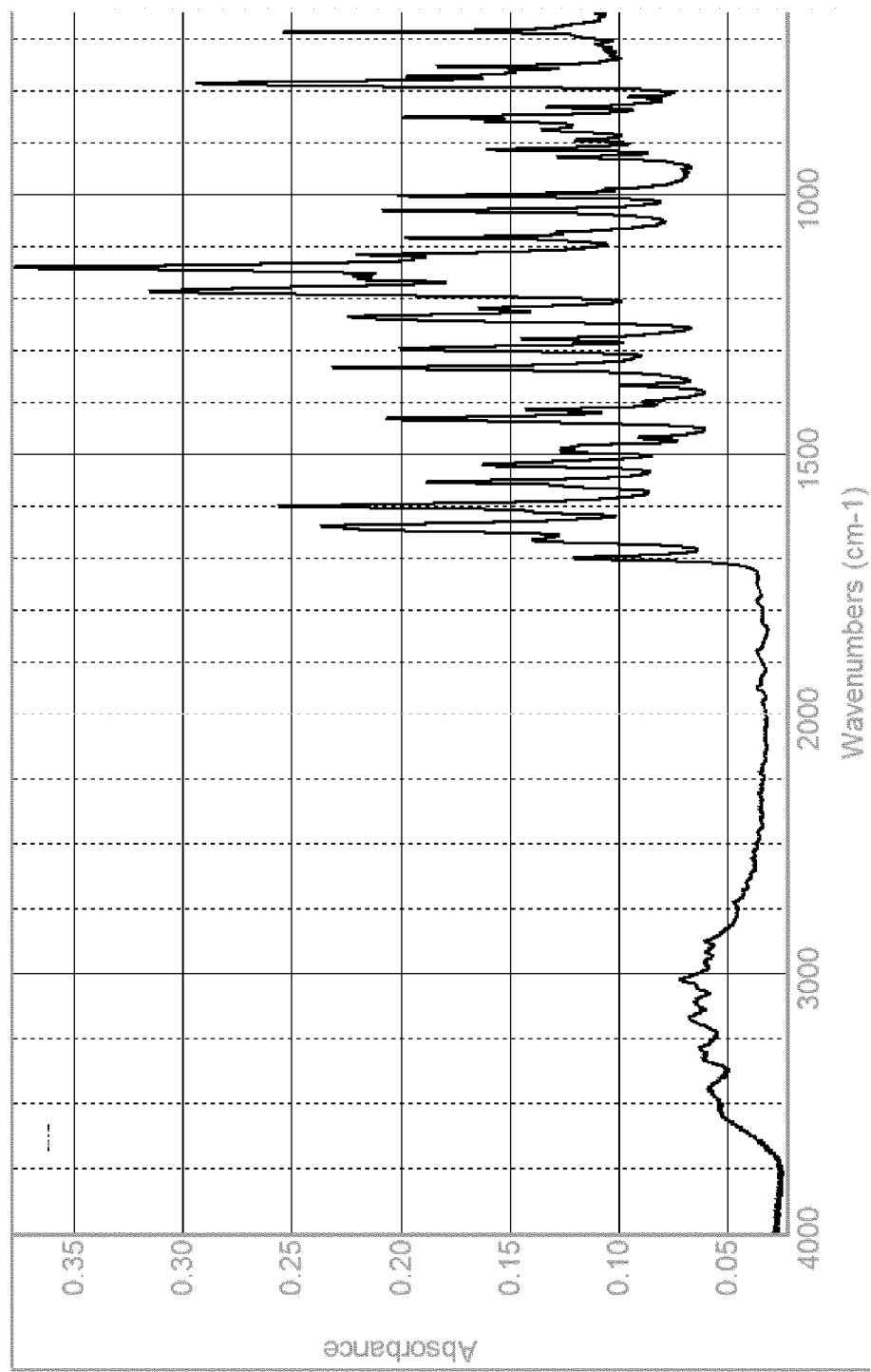
FIG. 6 is an infrared (IR) spectrum of Compound A monohydrate, Form III.

Form III may further be characterized by DVS. Form III may exhibit a DVS isotherm plot substantially as depicted in FIG. 4. The DVS isotherm plot of FIG. 4 shows Form III to be non-hygroscopic.

Preparation of Form III

Form III of Compound A monohydrate may be prepared by recrystallisation of Compound A or a hydrate or solvate thereof, for example Compound A hydrate Form I, from a suitably selected solvent mixture.

Form III of Compound A monohydrate may be prepared by a process comprising the steps of: a) adding Compound A, or a hydrate or solvate thereof, to a mixture of ethyl acetate and ethanol, and heating to a temperature in the range of from about 30° C. to solvent reflux temperature; b) adding water to the mixture and filtering off any precipitate, maintaining said temperature; c) adding n-heptane to the mixture, seeding with crystalline Form III, and maintaining said temperature; and d) cooling to room temperature, to yield a precipitate of the crystalline form; wherein the quantity of water is from about 0.1 w/w % to about 3 w/w %, relative to the total weight of solvent; in particular wherein the quantity of water is from about 1.0 w/w % to about 3 w/w %, relative to the total weight of solvent. In an embodiment, the quantity of water is at least 0.3 w/w %, in particular 0.4 w/w %, more in particular at least 0.8 w/w %, even more in particular at least 1.0 w/w %, relative to the total weight of solvent. In an embodiment, the quantity of water is at least 0.3 w/w %, in particular 0.4 w/w %, in particular at least 0.8 w/w %, even more in particular at least 1.0 w/w %, relative to the total mass of the reaction mixture. In an embodiment, the reaction mixture should contain an amount of water which exceeds 0.038 times the amount of Compound A.

In an embodiment, the quantity of water is maximum 3.0 w/w %, 2.5 w/w %, 2.0 w/w %, 1.5 w/w % or 1.0 w/w %, relative to the total weight of solvent.

In an embodiment, the quantity of water is 1.0 w/w % relative to the total weight of solvent.

In an embodiment, the quantity of water is from about 0.3 w/w % to about 1.5 w/w % relative to the total weight of solvent. In an embodiment, the quantity of water is from 0.3 w/w % to 1.5 w/w % relative to the total weight of solvent.

Alternatively, Form III of Compound A monohydrate may be prepared by a process comprising the steps of: a) Adding Compound A, or a hydrate or solvate thereof, to a mixture of water and isopropyl alcohol, and heating to a temperature in the range of from about 30° C. to solvent reflux temperature; b) adding n-heptane to the mixture, seeding with crystalline Form III, and maintaining said temperature; and c) cooling to room temperature, to yield a precipitate of the crystalline form; wherein the quantity of water is from about 1.0 w/w % to about 6.0 w/w %, relative to the total weight of solvent.

In an embodiment, the quantity of water is at least 2.0 w/w %, in particular 2.5 w/w %, more in particular at least 2.8 w/w %, even more in particular at least 3.0 w/w %, relative to the total weight of solvent. In an embodiment, the quantity of water is at least 2.0 w/w %, in particular 2.5 w/w %, more in particular at least 2.8 w/w %, even more in particular at least 3.0 w/w %, relative to the total mass of the reaction mixture.

In an embodiment, the quantity of water is maximum 5.5 w/w %, 5.0 w/w %, 4.5 w/w %, 4.0 w/w % or 3.5 w/w %, relative to the total weight of solvent.

In an embodiment, the quantity of water is 3.5 w/w % relative to the total weight of solvent.

In an embodiment, the quantity of water is from about 2.0 w/w % to about 5.0 w/w % relative to the total weight of solvent. In an embodiment, the quantity of water is from 2.0 w/w % to 5.0 w/w % relative to the total weight of solvent. A skilled person will realize that enough water must be present in the reaction mixture, and that the specific minimum amount of water is dependent on the amount of Compound A. In case the water content is too high, Form I of Compound A might form instead of Form III of Compound A, in which case the water content must be reduced. The total weight of solvent referred to in the descriptions hereabove, refers to the total weight of solvent in which the Form III of Compound A, or a hydrate (e.g. monohydrate) or solvate thereof, is soluble, not including the anti-solvents (water and n-heptane).

A skilled person will also understand that in case Compound A, used as a starting material in the preparation of Form III, is a hydrate, a certain amount of water will already be available in the system from the starting material. In case a non-hydrate solvate of Compound A is used instead as the starting material, it will be clear to a skilled person that more water will have to be added to the mixture to arrive at the required w/w %.

Compound A, or a hydrate or solvate thereof, may comprise crystalline hydrate Form I. The temperature to which the mixture is heated in the processes described herein may be from about 40° C. to about 55° C. In step a), the mixture may be heated for at least 30 mins or at least 1 hour. In the step wherein n-heptane is added, the crystalline Form III seed material may be added to the mixture following n-heptane addition and the temperature may be maintained for at least 4 hours. An additional portion of n-heptane may be added slowly over at least 5 hours, in particular over at least 8 hours, more in particular over at least 10 hours. In the step wherein the mixture is cooled to room temperature, the mixture may be stirred at room temperature for at least 12 hours.

The processes described herein may further comprise a step of filtering off the precipitate and washing said precipitate with n-heptane. The process may further comprise a step of drying the precipitate under vacuum, optionally at a temperature of from about 45° C. to about 55° C.

Form III of Compound A monohydrate may be prepared by a process comprising the steps of: a) adding Compound A, or a hydrate or solvate thereof, to ethyl acetate or isopropyl acetate; and b) stirring the resulting suspension at a temperature in the range of from about 30° C. to solvent reflux temperature, to yield a precipitate of crystalline monohydrate of Compound A, Form III. Compound A, or a hydrate or solvate thereof, may comprise crystalline hydrate Form I.

The temperature to which the mixture is heated may be from about 40° C. to about solvent reflux temperature or from about 50° C. to about solvent reflux temperature. The temperature to which the mixture is heated may be about 60° C. The suspension may be stirred for at least 1 day, at least 2 days, at least 3 days, at least 4 days, or at least 5 days.

The process may further comprise step c) of filtering off the precipitate. The process may further comprise step d) of drying the precipitate under vacuum, optionally at a temperature of from about 45° C. to about 55° C.

Alternatively, Form III of Compound A monohydrate may be prepared by a process comprising the steps of: a) adding Compound A, or a hydrate or solvate thereof, to a mixture of water and isopropyl alcohol; and b) stirring the resulting suspension at a temperature in the range of from about 30° C. to solvent reflux temperature, to yield a precipitate of crystalline monohydrate of Compound A, Form III. Compound A, or a hydrate or solvate thereof, may comprise crystalline hydrate Form I.

The temperature to which the mixture is heated may be from about 40° C. to about solvent reflux temperature or from about 50° C. to about solvent reflux temperature. The temperature to which the mixture is heated may be about 60° C. The suspension may be stirred for at least 1 day, at least 2 days, at least 3 days, at least 4 days, or at least 5 days.

The process may further comprise step c) of filtering off the precipitate. The process may further comprise step d) of drying the precipitate under vacuum, optionally at a temperature of from about 45° C. to about 55° C.

Compositions

Even though the compounds of embodiments of the present invention can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising crystalline Form III of Compound A monohydrate and at least one pharmaceutically acceptable carrier, pharmaceutically acceptable excipient, and/or pharmaceutically acceptable diluent.

By way of example, in the pharmaceutical compositions of embodiments of the present invention, crystalline Form III of Compound A monohydrate may be admixed with any suitable binder(s), lubricant(s), suspending agent(s), coating agent(s), solubilizing agent(s), and combinations thereof.

Solid oral dosage forms such as, tablets or capsules, containing the crystalline form of the present invention may be administered in at least one dosage form at a time, as appropriate. It is also possible to administer the crystalline form in sustained release formulations.

Additional oral forms in which the crystalline form may be administered include elixirs, solutions, syrups, and suspensions; each optionally containing flavouring agents and colouring agents.

Alternatively, the crystalline form can be administered by inhalation (intratracheal or intranasal) or in the form of a suppository or pessary, or may be applied topically in the form of a lotion, solution, cream, ointment or dusting powder. For example, it can be incorporated into a cream comprising, consisting of, and/or consisting essentially of an aqueous emulsion of polyethylene glycols or liquid paraffin. It can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as crystalline monohydrate Form III alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing the crystalline form as the active pharmaceutical ingredient can be prepared by mixing the crystalline form with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavouring agents, preservatives, stabilizers, colouring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of crystalline Form III of Compound A monohydrate or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active pharmaceutical ingredient in a regimen of about 1 to about (4×) per day for an average (70 kg) human; although, it is apparent to one skilled in the art that the therapeutically effective amount for said crystalline form will vary as will the diseases, syndromes, conditions, and disorders being treated.

For oral administration, a pharmaceutical composition is in particular provided in the form of tablets containing about 1.0, about 10, about 50, about 100, about 150, about 200, about 250, and about 500 milligrams of crystalline Form III of Compound A monohydrate.

For oral administration, a pharmaceutical composition is in particular provided in the form of capsules containing about 1.0, about 10, about 50, about 100, about 150, about 200, about 250, and about 500 milligrams of crystalline Form III of Compound A monohydrate.

An embodiment of the present invention is directed to a pharmaceutical composition for oral administration, comprising crystalline Form III of Compound A monohydrate in an amount of from about 25 mg to about 500 mg.

Advantageously, crystalline Form III of Compound A monohydrate may be administered in a single daily dose, or the total daily dosage may be administered in divided doses of two, three and 4× daily.

Optimal dosages of the crystalline form to be administered may be readily determined and will vary with the particular compound used, the mode of administration, the strength of the preparation, and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Methods of Treatment

Crystalline Form III of Compound A monohydrate may be administered in any of the foregoing compositions and dosage regimens or by means of those compositions and dosage regimens established in the art whenever use of the crystalline form is required for a subject in need thereof.

Crystalline Form III is useful in methods for treating, ameliorating and/or preventing a disease, a syndrome, a condition or a disorder that is affected by the inhibition of MALT1. Such methods comprise, consist of and/or consist essentially of administering to a subject, including an animal, a mammal, and a human in need of such treatment, amelioration and/or prevention, a therapeutically effective amount of crystalline Form III of Compound A monohydrate.

One embodiment of the present invention is directed to a method of treating a MALT1-dependent or MALT1-mediated disease or condition in a subject in need thereof, including an animal, a mammal, and a human in need of such treatment, comprising administering to the subject a therapeutically effective amount of crystalline Form III of Compound A monohydrate.

In another embodiment, the MALT1-dependent or MALT1-mediated disease or condition is selected from cancers of hematopoietic origin or solid tumors such as chronic myelogenous leukemia, myeloid leukemia, non-Hodgkin lymphoma, and other B cell lymphomas.

In particular, crystalline Form III of Compound A monohydrate is useful for treating or ameliorating diseases, syndromes, conditions, or disorders such as diffuse large B-cell lymphoma (DLBCL), mantle cell lymphoma (MCL), follicular lymphoma (FL), and mucosa-associated lymphoid tissue (MALT) lymphoma.

More particularly, crystalline Form III of Compound A monohydrate is useful for treating or ameliorating diffuse large B-cell lymphoma (DLBCL), mantle cell lymphoma (MCL), follicular lymphoma (FL), and mucosa-associated lymphoid tissue (MALT) lymphoma, comprising administering to a subject in need thereof a therapeutically effective amount said crystalline form.

Further, crystalline Form III of Compound A monohydrate is useful for treating or ameliorating an immunological disease, syndrome, disorder, or condition selected from the group consisting of rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD).

In an embodiment, cancers that may benefit from a treatment with crystalline Form III of Compound A monohydrate (a MALT1 inhibitor) include, but are not limited to, lymphomas, leukemias, carcinomas, and sarcomas, e.g. non-Hodgkin's lymphoma (NHL), B-cell NHL, diffuse large B-cell lymphoma (DLBCL), mantle cell lymphoma (MCL), follicular lymphoma (FL), mucosa-associated lymphoid tissue (MALT) lymphoma, marginal zone lymphoma, T-cell lymphoma, Hodgkin's lymphoma, Burkitt's lymphoma, multiple myeloma, chronic lymphocytic leukemia (CLL), small lymphocytic lymphoma (SLL), Waldenström macroglobulinemia, lymphoblastic T cell leukemia, chronic myelogenous leukemia (CML), hairy-cell leukemia, acute lymphoblastic T cell leukemia, plasmacytoma, immunoblastic large cell leukemia, megakaryoblastic leukemia, acute megakaryocyte leukemia, promyelocytic leukemia, erythroleukemia, brain (gliomas), glioblastomas, breast cancer, colorectal/colon cancer, prostate cancer, lung cancer including non-small-cell, gastric cancer, endometrial cancer, melanoma, pancreatic cancer, liver cancer, kidney cancer, squamous cell carcinoma, ovarian cancer, sarcoma, osteosarcoma, thyroid cancer, bladder cancer, head & neck cancer, testicular cancer, Ewing's sarcoma, rhabdomyosarcoma, medulloblastoma, neuroblastoma, cervical cancer, renal cancer, urothelial cancer, vulval cancer, esophageal cancer, salivary gland cancer, nasopharangeal cancer, buccal cancer, cancer of the mouth, and GIST (gastrointestinal stromal tumor).

In another embodiment, the crystalline Form III of Compound A monohydrate may be used for the treatment of immunological diseases including, but not limited to, autoimmune and inflammatory disorders, e.g. arthritis, inflammatory bowel disease, gastritis, ankylosing spondylitis, ulcerative colitis, pancreatitis, Crohn's disease, celiac disease, multiple sclerosis, systemic lupus erythematosus, lupus nephritis, rheumatic fever, gout, organ or transplant rejection, chronic allograft rejection, acute or chronic graft-versus-host disease, dermatitis including atopic, dermatomyositis, psoriasis, Behcet's diseases, uveitis, myasthenia gravis, Grave's disease, Hashimoto thyroiditis, Sjoergen's syndrome, blistering disorders, antibody-mediated vasculitis syndromes, immune-complex vasculitides, allergic disorders, asthma, bronchitis, chronic obstructive pulmonary disease (COPD), cystic fibrosis, pneumonia, pulmonary diseases including oedema, embolism, fibrosis, sarcoidosis, hypertension and emphysema, silicosis, respiratory failure, acute respiratory distress syndrome, BENTA disease, berylliosis, and polymyositis.

One embodiment of the present invention is directed to a method of treating a disease, syndrome, condition, or disorder, wherein said disease, syndrome, condition, or disorder is affected by the inhibition of MALT1, comprising administering to a subject in need thereof a therapeutically effective amount of crystalline Form III of Compound A monohydrate.

In a further embodiment, the disease, syndrome, condition, or disorder is selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD).

In a further embodiment, the disease, syndrome, condition, or disorder is selected from the group consisting of diffuse large B-cell lymphoma (DLBCL), mantle cell lymphoma (MCL), follicular lymphoma (FL), mucosa-associated lymphoid tissue (MALT) lymphoma, marginal zone lymphoma, chronic lymphocytic leukemia (CLL), small lymphocytic lymphoma (SLL), and Waldenström macroglobulinemia.

In one embodiment, the present invention is directed to a method of treating a disease, syndrome, condition, or disorder selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD), comprising administering to a subject in need thereof a therapeutically effective amount of crystalline Form III of Compound A monohydrate.

In another embodiment, the present invention is directed to a method of treating a disease, syndrome, condition, or disorder selected from the group consisting of diffuse large B-cell lymphoma (DLBCL), mantle cell lymphoma (MCL), follicular lymphoma (FL), mucosa-associated lymphoid tissue (MALT) lymphoma, marginal zone lymphoma, chronic lymphocytic leukemia (CLL), small lymphocytic lymphoma (SLL), and Waldenström macroglobulinemia, comprising administering to a subject in need thereof a therapeutically effective amount of crystalline Form III of Compound A monohydrate. In a further embodiment, the disease, syndrome, condition, or disorder is non-Hodgkin's lymphoma (NHL). In a further embodiment, the non-Hodgkin's lymphoma (NHL) is B-cell NHL.

In another embodiment, the present invention is directed to crystalline Form III of Compound A monohydrate for the preparation of a medicament for treating a disease, syndrome, disorder or condition selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD), in a subject in need thereof.

In another embodiment, the present invention is directed to crystalline Form III of Compound A monohydrate for the preparation of a medicament for treating a disease, syndrome, condition, or disorder selected from the group consisting of diffuse large B-cell lymphoma (DLBCL), mantle cell lymphoma (MCL), follicular lymphoma (FL), mucosa-associated lymphoid tissue (MALT) lymphoma, marginal zone lymphoma, chronic lymphocytic leukemia (CLL), small lymphocytic lymphoma (SLL), and Waldenström macroglobulinemia, in a subject in need thereof. In a further embodiment, the disease, syndrome, condition, or disorder is non-Hodgkin's lymphoma (NHL). In a further embodiment, the non-Hodgkin's lymphoma (NHL) is B-cell NHL.

In another embodiment, crystalline Form III of Compound A monohydrate is for use in a method for treating a disorder selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD), in a subject in need thereof.

In another embodiment, crystalline Form III of Compound A monohydrate is for use in a method for treating a disease, syndrome, condition, or disorder selected from the group consisting of diffuse large B-cell lymphoma (DLBCL), mantle cell lymphoma (MCL), follicular lymphoma (FL), mucosa-associated lymphoid tissue (MALT) lymphoma, marginal zone lymphoma, chronic lymphocytic leukemia (CLL), small lymphocytic lymphoma (SLL), and Waldenström macroglobulinemia, in a subject in need thereof. In a further embodiment, the disease, syndrome, condition, or disorder is non-Hodgkin's lymphoma (NHL), in a subject in need thereof. In a further embodiment, the non-Hodgkin's lymphoma (NHL) is B-cell NHL.

In another embodiment, crystalline Form III of Compound A monohydrate is for use in the treatment of a disorder selected from the group consisting of diffuse large B-cell lymphoma (DLBCL), mantle cell lymphoma (MCL), follicular lymphoma (FL), and mucosa-associated lymphoid tissue (MALT) lymphoma rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD), in a subject in need thereof.

In another embodiment, crystalline Form III of Compound A monohydrate is for use in the treatment of a disease, syndrome, condition, or disorder selected from the group consisting of diffuse large B-cell lymphoma (DLBCL), mantle cell lymphoma (MCL), follicular lymphoma (FL), mucosa-associated lymphoid tissue (MALT) lymphoma, marginal zone lymphoma, chronic lymphocytic leukemia (CLL), small lymphocytic lymphoma (SLL), and Waldenström macroglobulinemia, in a subject in need thereof. In a further embodiment, the disease, syndrome, condition, or disorder is non-Hodgkin's lymphoma (NHL), in a subject in need thereof. In a further embodiment, the non-Hodgkin's lymphoma (NHL) is B-cell NHL.

In another embodiment, crystalline Form III of Compound A monohydrate is for use in the treatment of a disease, syndrome, condition, or disorder in a subject in need thereof, wherein said disease, syndrome, condition, or disorder is affected by the inhibition of MALT1.

In another embodiment of the present invention, crystalline Form III of Compound A monohydrate may be employed in combination with one or more other medicinal agents, more particularly with other anti-cancer agents, e.g. chemotherapeutic, anti-proliferative or immunomodulating agents, or with adjuvants in cancer therapy, e.g. immunosuppressive or anti-inflammatory agents.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All possible combinations of the above-indicated embodiments are considered to be embraced within the scope of this invention.

Reference is now made to the following examples, which illustrate the invention in a non-limiting fashion.

EXAMPLES

X-ray powder diffraction (XRPD) analysis was carried out on a Bruker (D8 Advance) X-ray powder diffractometer. The compound was spread on a mono-crystalline silicon plate and pressed gently to be flat and homogeneous for testing.

Samples were run on XRPD using the method below:
Tube: Cu: K-Alpha (λ=1.54056 Å)
Generator: Voltage: 40 kV; Current: 40 mA
Detector: PSD: LynxEye
Divergence Slit: 0.60 mm; Primary Soller Slit: 2.5 deg.
Detector Slit: 10.50 mm; Antiscatter Slit: 7.10 mm
Sec. Soller Slit: 2.5 deg.
Scan type: Locked Coupled
Scan mode: Continuous Scan
Scan parameter: Scan axis: 2-Theta/Theta
Scan Scope: 3 to 50 deg.; Step size: 0.02 deg.
Time/step: 0.12 s
Sample rotation: 60 rpm
Scanning rate: 10 deg/min One skilled in the art will recognize that diffraction patterns and peak positions are typically substantially independent of the diffractometer used and whether a specific calibration method is utilized. Typically, the peak positions may differ by about ±0.2° two theta, or less. The intensities (and relative intensities) of each specific diffraction peak may also vary as a function of various factors, including, but not limited to particle size, orientation, sample purity, etc. However the skilled person will be able to differentiate the between Compound A, hydrate Form I and Compound A, monohydrate Form III.

Thermogravimetric analysis (TGA) was carried out on a TA Instruments Q5000 IR thermogravimetric analyzer equipped with a Hiden quantitative gas analysis unit. The sample was placed in a standard platinum sample pan from TA instruments after it was tared. The sample was scanned from 25° to 300° C. with a programmed heating rate of 20° C./min.

The moisture sorption analysis (DVS) was performed using a Surface Measurement Systems Advantage-1 dynamic vapor sorption apparatus. The moisture profile was evaluated by monitoring vapor adsorption/desorption over the range of 0 to 95% relative humidity at 25° C. The moisture profile consisted of 2 cycles of vapor adsorption/desorption.

Infrared (IR) spectroscopy was carried out on Nicolet 6700FT-IR Spectrometer with a micro ATR accessory.

Example 1: Preparation of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) hydrate, Form I Compound A hydrate was prepared by analogy to the synthesis method as described in Example 158 of WO 2018/119036. The compound prepared by this method was confirmed to be a hydrate crystalline form, Form I.

Form I was characterised using X-ray powder diffraction (XRPD), differential scanning calorimetry (DSC), thermal gravimetric analysis (TGA), dynamic vapor sorption (DVS), and IR spectroscopy (FIGS. 7 to 12).

The X-ray powder diffraction pattern of Form I (FIG. 7) shows distinct diffraction peaks, without the presence of a halo, indicating that this is a crystalline product.

Table 1 provides peak listings and relative intensity for the XPRD of Compound A hydrate, Form I (FIG. 7).

TABLE 1

| Pos. [°2Th.] | Rel. Int. [%] |
| --- | --- |
| 3.3492 | 39.37 |
| 6.6640 | 4.90 |
| 8.3921 | 99.18 |
| 9.5561 | 2.00 |
| 9.9822 | 17.19 |
| 10.4253 | 1.40 |
| 10.7270 | 21.94 |
| 12.0003 | 10.48 |
| 12.2582 | 8.63 |
| 12.6973 | 75.08 |
| 13.3111 | 100.00 |
| 13.5391 | 25.04 |
| 14.0837 | 34.93 |
| 14.5855 | 33.39 |
| 15.3831 | 8.76 |
| 15.5724 | 12.24 |
| 15.9676 | 9.12 |
| 16.7336 | 64.64 |
| 17.4857 | 6.14 |
| 18.0702 | 31.51 |
| 18.3862 | 8.90 |
| 19.2183 | 16.27 |
| 20.0081 | 39.14 |
| 20.3419 | 26.48 |
| 21.1256 | 34.24 |
| 21.3242 | 15.79 |
| 22.0092 | 35.62 |
| 22.5028 | 16.08 |
| 23.1445 | 7.75 |
| 23.4107 | 11.70 |
| 23.8241 | 9.17 |
| 24.3918 | 19.32 |
| 24.5913 | 18.26 |
| 24.9140 | 46.75 |
| 25.3974 | 32.79 |
| 25.5768 | 43.71 |
| 26.1570 | 11.50 |
| 26.7323 | 3.55 |
| 27.2280 | 21.80 |
| 27.5416 | 32.47 |
| 27.8348 | 16.14 |
| 28.0704 | 8.75 |
| 28.6818 | 11.22 |
| 29.3712 | 4.98 |
| 30.3808 | 4.04 |
| 31.2917 | 10.24 |
| 31.5862 | 11.98 |
| 32.9442 | 5.01 |
| 33.6350 | 4.99 |
| 33.9874 | 2.68 |
| 34.4781 | 3.01 |
| 34.8120 | 4.21 |
| 35.6513 | 3.06 |
| 37.1454 | 3.83 |
| 38.9841 | 1.18 |
| 39.4671 | 1.81 |
| 40.6150 | 4.58 |
| 42.5268 | 2.93 |
| 43.4580 | 2.63 |
| 44.1621 | 1.20 |
| 45.6961 | 2.04 |
| 46.7044 | 4.03 |
| 48.7494 | 8.95 |
| 48.8885 | 4.57 |
| 49.8753 | 4.63 |

The DSC curve of Form I (FIG. 8) shows a broad endothermic signal at 98.7° C. (142 J/g), with an onset temperature of 66.3° C., due to the dehydration of the hydrate. A second endothermic signal is observed at 157.0° C. (17 J/g), with an onset temperature of 145.2° C., and corresponds to melting of the dehydrated form.

The TGA curve of Form I (FIG. 9) shows a weight loss of 4.7% from RT up to 82° C. due to evaporation of solvent (water) present. A weight loss of 0.4% was registered between 82-122° C. and corresponds to further evaporation of solvent.

Figure 11:
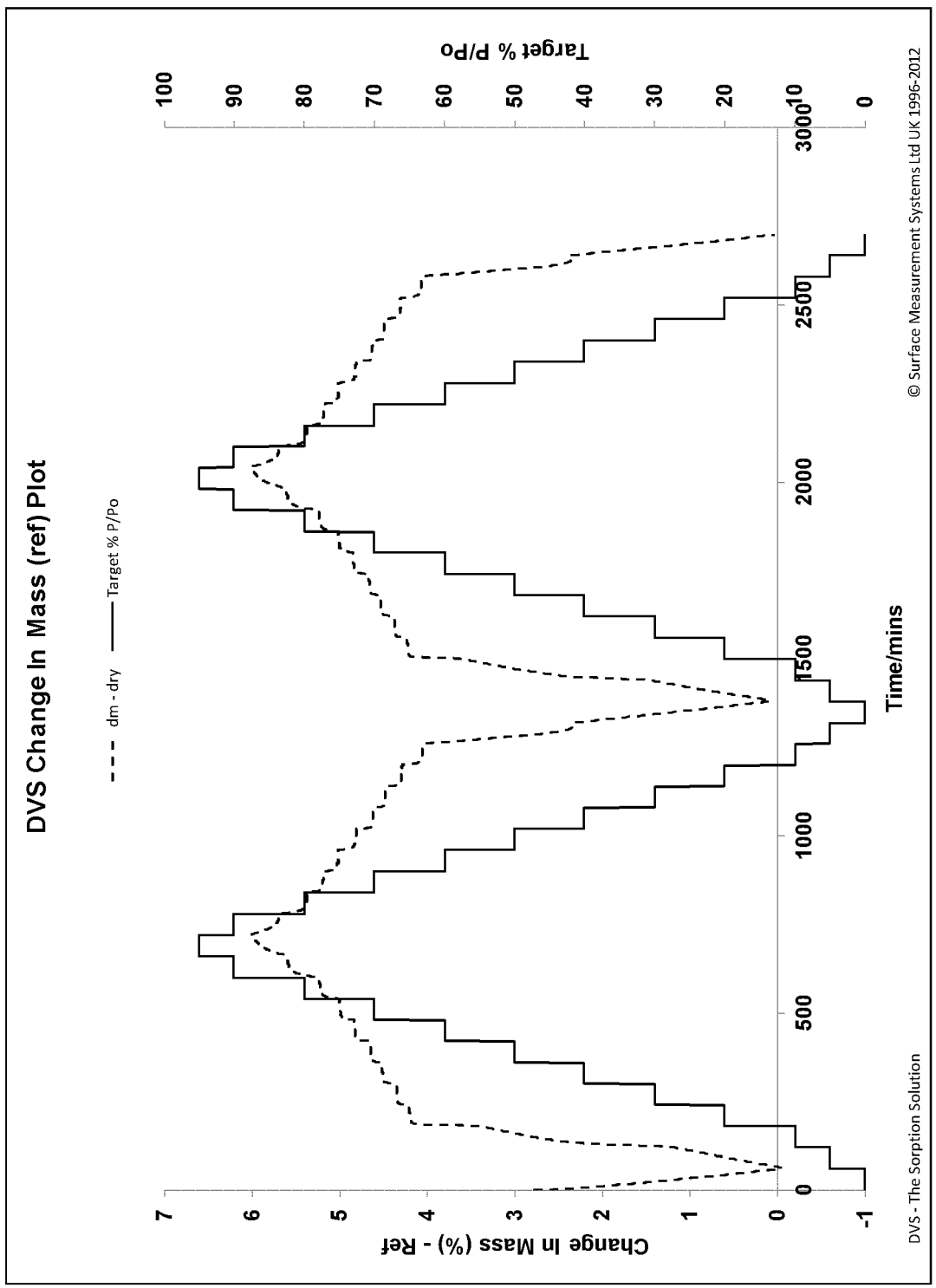
FIG. 11 is an DVS change in mass plot of Compound A hydrate, Form I.
Figure 12:
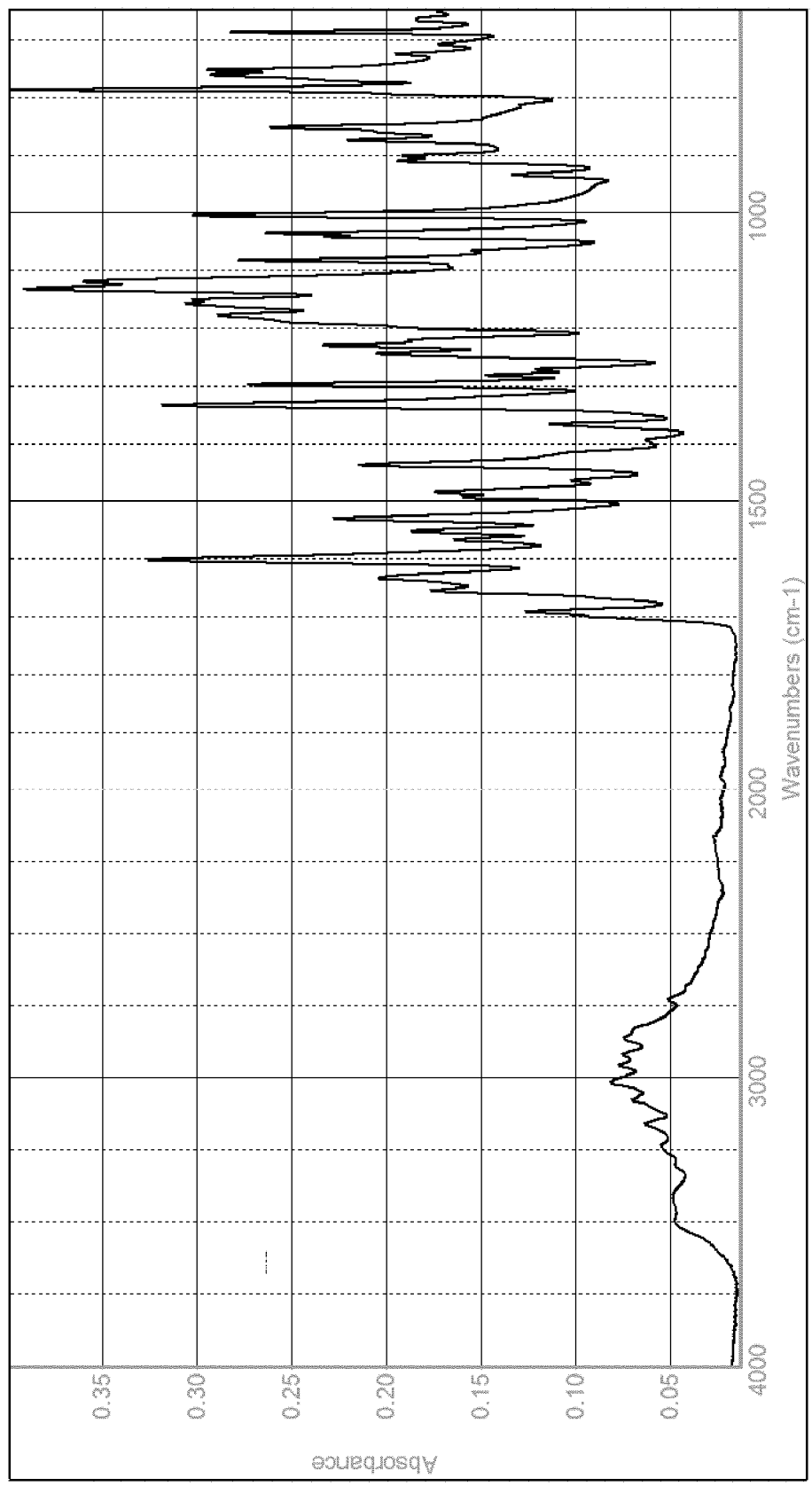
FIG. 12 is an IR spectrum of Compound A hydrate, Form I.

The DVS change in mass plot of Form I (FIG. 11) shows a ~2.7% weight loss during the initial drying step. The compound adsorbs and desorbs water quickly in the humidity range of 0-20% RH (relative humidity) (FIGS. 10 and 11). It adsorbs up to 4.1-4.2% moisture (between 0-20% RH) depending on the atmospheric humidity and dries completely during the desorption cycle. In the humidity range of 20-95% RH, the compound adsorbs and desorbs slowly and reversibly, with 1.8% moisture adsorption and desorption. The XRPD pattern and IR spectrum of the fraction obtained after the DVS test were comparable to the starting material. No indication of a solid-state form change was observed.

This data indicates that the hydration water in Form I is loosely bound and is lost at RH of 20% and less.

Example 2: Preparation of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate, Form III seed material Approx. 200 mg of Compound A, hydrate Form I obtained by Example 1, was added to 400-800 µl of either ethyl acetate or isopropyl acetate and the resulting suspension stirred at 60° C. for 5 days. The precipitate was then filtered and dried under vacuum at 50° C. for 24 hours to yield crystalline monohydrate of Compound A, Form III.

Example 3: Preparation of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate, Form III 1-(1-oxo-1,2-dihydroisoquinolin-5-yl)-5-(trifluoromethyl)-N-[2-(trifluoromethyl)pyridin-4-yl]-1H-pyrazole-4-carboxamide (100 g) obtained by a procedure analogous to the synthesis method as described in Example 158 of WO 2018/119036 was charged in a flask (R1) together with ethanol (150-170 mL) and ethyl acetate (80-100 mL). The obtained mixture was heated to 400-50° C. and stirred for 0.5-2 hours. Water (4-7 mL) was then added and the water content was measured by Karl Fischer titration. The content of R1 was warmed to 40°-55° C. and filtered into a second flask (R2) pre-heated at 40°-55° C. R1 was rinsed with ethyl acetate (80-100 mL) at 40°-50° C. and the content filtered into R2. n-Heptane (340-410 mL) was charged into R2 in about 20-40 min. maintaining 40°-45° C. The obtained solution was seeded with 1.9-2.1 g of Compound A monohydrate, Form III (obtained from Example 2) and the obtained mixture was stirred at 40°-55° C. for 4-8 hours. n-Heptane (680-750 mL) was added in 10-15 hours maintaining 400-55° C.; the obtained mixture was stirred for additional 2-5 hours at 40°-55° C., then it was cooled down to 20°-25° C. for 7-13 hours. The suspension was stirred at 20°-25° C. for 12-18 h, then it was filtered and washed with n-heptane (180-250 mL). After drying under vacuum at 45°-55° C. for 15-22 hours, 1-(1-oxo-1,2-dihydroisoquinolin-5-yl)-5-(trifluoromethyl)-N-[2-(trifluoromethyl)pyridin-4-yl]-1H-pyrazole-4-carboxamide monohydrate (Form III) was obtained with an 80% yield.

Example 3b: Preparation of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate, Form III 1-(1-oxo-1,2-dihydroisoquinolin-5-yl)-5-(trifluoromethyl)-N-[2-(trifluoromethyl)pyridin-4-yl]-1H-pyrazole-4-carboxamide (25 g) obtained by a procedure analogous to the synthesis method as described in Example 158 of WO 2018/119036 was charged in a flask (R1) together with water (2.5-4.5 mL) and isopropyl alcohol (IPA) (100 mL). The obtained mixture was heated to 50° C. and stirred for 0.5-2 hours. n-Heptane (125 mL) was charged into R1. The obtained solution was seeded with 500 mg of Compound A monohydrate, Form III (obtained from Example 2) and the obtained mixture was stirred at 50° C. for 72 hours. n-Heptane (275 mL) was added in 12 hours maintaining 50° C.; the obtained mixture was stirred for additional 58 hours at 50° C., then it was cooled down to 20°-25° C. for 2 hours. The suspension was stirred at 20°-25° C. for 94 h, then it was filtered and washed with n-heptane (100 mL). After drying under vacuum at 50° C. for 24 hours, 1-(1-oxo-1,2-dihydroisoquinolin-5-yl)-5-(trifluoromethyl)-N-[2-(trifluoromethyl)pyridin-4-yl]-1H-pyrazole-4-carboxamide monohydrate (Form III) was obtained with an 90% yield.

Form III was characterised using X-ray powder diffraction (XRPD), differential scanning calorimetry (DSC), thermal gravimetric analysis (TGA), dynamic vapor sorption (DVS) and IR spectroscopy—see FIGS. 1 to 6.

The X-ray powder diffraction pattern of Form III (FIG. 1) shows distinct diffraction peaks, without the presence of a halo, indicating that this compound is present as a crystalline product.

Table 2 provides peak listings and relative intensities for the XPRD of Compound A monohydrate, Form III (FIG. 1).

TABLE 2

| Pos. [°2Th.] | Rel. Int. [%] |
|---|---|
| 8.2904 | 25.26 |
| 8.6250 | 23.96 |
| 9.3485 | 2.24 |
| 11.4511 | 14.20 |
| 12.5682 | 4.31 |
| 13.6202 | 45.95 |
| 13.9754 | 21.49 |
| 15.4397 | 41.22 |
| 15.8867 | 3.10 |
| 16.4426 | 100.00 |
| 16.6283 | 17.71 |
| 17.5110 | 14.58 |
| 17.9121 | 41.41 |
| 18.6250 | 4.18 |
| 19.6673 | 14.48 |
| 21.5675 | 11.28 |
| 21.9258 | 14.96 |
| 22.1775 | 15.69 |
| 22.5940 | 41.75 |
| 23.6809 | 85.80 |
| 24.0437 | 15.69 |
| 24.5412 | 27.75 |
| 25.1642 | 29.90 |
| 25.7310 | 49.96 |
| 27.1482 | 38.49 |
| 27.6772 | 10.70 |
| 27.9857 | 5.32 |
| 29.0996 | 7.66 |
| 29.3985 | 10.88 |
| 29.9267 | 20.17 |
| 30.9874 | 5.22 |
| 31.8056 | 12.06 |
| 32.8799 | 7.23 |
| 33.1991 | 5.73 |
| 34.4861 | 6.97 |
| 36.3854 | 7.95 |
| 36.6246 | 4.89 |
| 37.3258 | 7.90 |
| 37.8748 | 7.87 |
| 38.3143 | 5.55 |
| 40.8261 | 2.60 |
| 42.4567 | 3.57 |

TABLE 2-continued

| Pos. [°2Th.] | Rel. Int. [%] |
|---|---|
| 43.2056 | 2.48 |
| 43.7464 | 4.48 |
| 45.0366 | 1.28 |
| 46.0177 | 2.48 |
| 48.3545 | 1.47 |

The DSC curve of Form III (FIG. 2) shows the collapsing and liquefying of the crystalline product as an endothermal signal with an onset temperature of 142° C. and a maximum at 158° C. (145.9 J/g).

The TGA curve of Form III (FIG. 3) shows a total weight loss of 3.9% from RT up to 180° C. due to evaporation of bound solvent.

The hygroscopic character of Form III was assessed by dynamic vapor sorption (DVS) analysis. Form III is non-hygroscopic, as can be seen in the DVS plots in FIGS. 4 and 5. Form III does not lose water at low RH (relative humidity) conditions, unlike Form I. The XRPD pattern and IR spectrum of the fraction obtained after the DVS test was comparable to the starting material. No indication of a solid-state form change was observed.

Example 4: Physical Stability Study of Compound A Monohydrate, Form III

The physical stability of Compound A monohydrate, Form III with respect to water loss or uptake was tested.

For the initial study, 0.5 g samples of monohydrate Form III were placed in double antistatic colourless LDPE bags and sealed.

For the long-term study (stability after 1 month and 3 months), 1.5 g samples of monohydrate Form III were placed in double antistatic colourless LDPE bags and sealed. The samples were stored at 30±2° C./75±5% RH and 40±2° C./75±5% RH in cardboard drums.

For the photostability study, 1.5 g of monohydrate Form III was placed into a petri dish and spread into a layer of no more than 3 mm thick. The petri dish was covered with quartz coverslips and sealed with parafilm. The photostability testing was carried out in line with ICH Q1B option 2 (ICH Harmonised Tripartite Guideline, Stability testing: Photostability testing of new drug substances and products, Q1B, Step 4 version, 6 Nov. 1996). Photostability samples were stored under separate lamps emitting visible and UV-A light, such that the total exposure was not less than 1.2 million lux hours and 200 Watt hours/m², respectively. The water content of each of the samples was determined using a vaporized coulometric Karl Fischer method, in accordance with the US Pharmacopeia (USP <921> method IC; most recently appeared in Pharmacopeial Forum: Volume No. 38(1); Page information USP42/NF37-7092) and European Pharmacopeia 2.5.32 (Edition 10.0).

The results (Table 3) demonstrate that monohydrate Form III is non-hygroscopic.

TABLE 3

| Storage condition | Storage time | Water content (%) |
|---|---|---|
| — | Initial | 3.4 |
| 1 × ICH option 2 | — | 3.4 |
| 30° C./75% RH | 1 month | 3.3 |
|  | 3 months | 3.8 |

TABLE 3-continued

| Storage condition | Storage time | Water content (%) |
|---|---|---|
| 40° C./75% RH | 1 month | 3.3 |
|  | 3 months | 3.2 |

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention and that embodiments within the scope of these claims and their equivalents be covered thereby.

We claim:

1. A crystalline form of 1-(1-oxo-1,2-dihydroisoquinolin-5-yl)-5-(trifluoromethyl)-N-[2-(trifluoromethyl)pyridin-4-yl]-1H-pyrazole-4-carboxamide (Compound A) monohydrate:

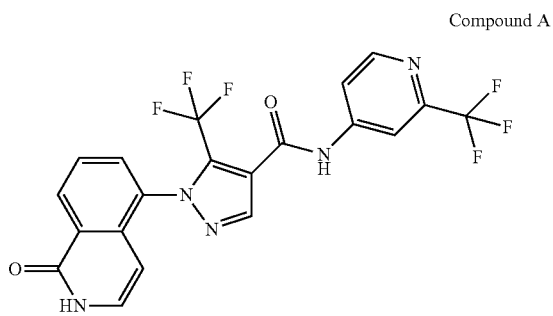 [SMILES: O=C(Nc1ccnc(C(F)(F)F)c1)c1cnn(-c2cccc3c(=O)[nH]ccc23)c1C(F)(F)F]

Compound A wherein the crystalline form is Form III, producing an X-ray powder diffraction pattern comprising peaks at 16.4, 23.7 and 25.7 degrees two theta±0.2 degrees two theta.

2. The crystalline form of claim 1, wherein the X-ray powder diffraction pattern further comprises peaks at 13.6, 17.9, 22.6, 24.5, 25.2 and 27.1 degrees two theta±0.2 degrees two theta.

3. The crystalline form of claim 2, wherein the X-ray powder diffraction pattern further comprises at least one peak selected from 8.3, 8.6, 11.5, 14.0, 15.4, 17.5, 19.7, 22.0, 22.2, 24.0 and 29.9 degrees two theta±0.2 degrees two theta.

4. The crystalline form of claim 2, wherein the X-ray powder diffraction pattern further comprises peaks at 8.3, 8.6, 11.5, 14.0, 15.4, 17.5, 19.7, 22.0, 22.2, 24.0 and 29.9 degrees two theta±0.2 degrees two theta.

5. The crystalline form of claim 1, further characterized by a differential scanning calorimetry thermogram comprising an endotherm with an onset temperature of about 142° C. and/or a peak temperature at about 158° C.

6. A pharmaceutical composition comprising the crystalline form of claim 1 and at least one of a pharmaceutically acceptable carrier, a pharmaceutically acceptable excipient, and a pharmaceutically acceptable diluent.

7. The pharmaceutical composition of claim 6, wherein the composition is a solid oral dosage form.

8. The pharmaceutical composition of claim 6, wherein the composition is a syrup, elixir, or suspension.

9. A method of treating a cancer or an immunological disease comprises administering to a subject in need thereof a therapeutically effective amount of the crystalline form of claim 1.

10. The method of claim 9, wherein the cancer or the immunological disease is selected from the group consisting of diffuse large B-cell lymphoma (DLBCL), mantle cell lymphoma (MCL), follicular lymphoma (FL), and mucosa-associated lymphoid tissue (MALT) lymphoma, rheumatoid arthritis (RA), psoriatic arthritis (PsA), psoriasis (Pso), ulcerative colitis (UC), Crohn's disease, systemic lupus erythematosus (SLE), asthma, and chronic obstructive pulmonary disease (COPD).

11. A process for preparing the crystalline form of claim 1, comprising the step of recrystallising Compound A, wherein the recrystallisation comprises the steps of:
   a) adding Compound A, or a hydrate or solvate thereof, to a mixture of ethyl acetate and ethanol, and heating to a temperature in the range of from about 30° C. to solvent reflux temperature;
   b) adding water to the mixture and filtering off any precipitate, maintaining said temperature;
   c) adding n-heptane to the mixture, seeding with crystalline Form III, and maintaining said temperature; and
   d) cooling to room temperature, to yield a precipitate of the crystalline form of claim 1;
wherein the quantity of water is from about 0.1 w/w % to about 3.0 w/w %, relative to the total weight of solvent.

12. The process of claim 11, wherein the temperature is from about 40° C. to about 55° C.

13. A process for preparing the crystalline form of claim 1, comprising the step of recrystallising Compound A, wherein the recrystallisation comprises the steps of:
   a) adding Compound A, or a hydrate or solvate thereof, to a mixture of water and isopropyl alcohol, and heating to a temperature in the range of from about 30° C. to solvent reflux temperature;
   b) adding n-heptane to the mixture, seeding with crystalline Form III, and maintaining said temperature; and
   c) cooling to room temperature, to yield a precipitate of the crystalline form of claim 1;
wherein the quantity of water is from about 1.0 w/w % to about 6.0 w/w %, relative to the total weight of solvent.

* * * * *